US008206718B2

(12) United States Patent
Lo et al.

(10) Patent No.: US 8,206,718 B2
(45) Date of Patent: Jun. 26, 2012

(54) EXPRESSION AND EXPORT OF ANGIOGENESIS INHIBITORS AS IMMUNOFUSINS

(75) Inventors: Kin-Ming Lo, Lexington, MA (US); Yue Li, Bedford, MA (US); Stephen D. Gillies, Carlisle, MA (US)

(73) Assignee: Merck Patent GmbH, Darmstadt (DE)

( * ) Notice: Subject to any disclaimer, the term of this patent is extended or adjusted under 35 U.S.C. 154(b) by 1448 days.

(21) Appl. No.: 11/475,627

(22) Filed: Jun. 27, 2006

(65) Prior Publication Data

US 2007/0009538 A1 Jan. 11, 2007

Related U.S. Application Data

(63) Continuation of application No. 10/292,418, filed on Nov. 12, 2002, now abandoned, which is a continuation of application No. 09/383,315, filed on Aug. 25, 1999, now abandoned.

(60) Provisional application No. 60/097,883, filed on Aug. 25, 1998.

(51) Int. Cl.
*A61K 39/00* (2006.01)
*C07K 14/00* (2006.01)

(52) U.S. Cl. .................. 424/184.1; 424/185.1; 530/356

(58) Field of Classification Search ........................ None
See application file for complete search history.

(56) References Cited

U.S. PATENT DOCUMENTS

| | | | | |
|---|---|---|---|---|
| 5,541,087 | A * | 7/1996 | Lo et al. | 435/69.7 |
| 5,854,205 | A * | 12/1998 | O'Reilly et al. | 514/2 |
| 2003/0114370 | A1* | 6/2003 | Folkman et al. | 514/12 |
| 2004/0033210 | A1* | 2/2004 | Gillies | 424/85.1 |
| 2004/0180035 | A1* | 9/2004 | Gillies | 424/85.1 |

OTHER PUBLICATIONS

O'Reilly MS et al. Endostatin: An Endogenous Inhibitor of Angiogenesis and Tumor Growth. Cell, vol. 88, Issue 2, 277-285, Jan. 24, 1997.*
Kuo et al. J. Cell Biol., 2001 ; 152:1233-1246.*
Bergers et al. Science, 1999; 284:808-812.*

* cited by examiner

*Primary Examiner* — Maher Haddad
(74) *Attorney, Agent, or Firm* — Olson & Cepuritis, Ltd.

(57) ABSTRACT

A homodimeric protein of the invention has angiogenesis inhibiting activity. The homodimeric protein consists of two identical fusion proteins bound together as a homodimer. Each fusion protein comprises an immunoglobulin Fc region and a first target protein linked to the immunoglobulin Fc region. The first target protein has an angiogenesis inhibiting activity of angiostatin or endostatin, and is selected from the group consisting of a plasminogen fragment and a collagen XVIII fragment. The immunoglobulin Fc region comprises a hinge region, a CH2 region, and a CH3 region.

4 Claims, 1 Drawing Sheet

EXPRESSION AND EXPORT OF ANGIOGENESIS INHIBITORS AS IMMUNOFUSINS

CROSS-REFERENCE TO RELATED APPLICATIONS

This is a continuation of U.S. application Ser. No. 10/292,418, filed on Nov. 12, 2002, now abandoned, which is a continuation of U.S. application Ser. No. 09/383,315, filed on Aug. 25, 1999, now abandoned, which claims the benefit of U.S. Provisional Application Ser. No. 60/097,883, filed on Aug. 25, 1998, each of which is incorporated herein by reference.

FIELD OF THE INVENTION

This invention relates generally to methods and compositions for making and using fusion proteins containing an angiogenesis inhibitor. More particularly, the invention relates to methods and compositions for making and using fusion proteins called immunofusins which contain an immunoglobulin Fc region and an angiogenesis inhibitor.

BACKGROUND OF THE INVENTION

Two potent angiogenesis inhibitors, angiostatin (O'Reilly et al. (1994) Cell 79:315) and endostatin (O'Reilly et al. (1997) Cell 88:277), were discovered and found to be generated naturally by primary tumors. Both proteins are specific inhibitors of endothelial cell proliferation and inhibit tumor growth by blocking angiogenesis, the formation of new blood vessels that nourish tumors. Studies have shown that these angiogenesis inhibitors are non-toxic even at very high doses and that they may suppressed the growth of metastases and primary tumors may regress to a dormant microscopic state. Both inhibitors were identified as proteolytic fragments of much larger intact molecules. Angiostatin was found to be a fragment of plasminogen, and endostatin a fragment of collagen XVIII.

These two proteins have generated great interest in the cancer area because they have been shown to suppress the growth of many different types of tumors in mice, with no obvious side effects or drug resistance. Traditional chemotherapy generally leads to acquired drug resistance caused primarily by the genetic instability of cancer cells. Rather than targeting cancer cells, therapies using angiogenesis inhibitors target the normal endothelial cells, which support the growth of the tumor. Because endothelial cells are genetically stable, it is possible that angiogenesis inhibitor therapies may result in less drug resistance. Studies indicate that drug resistance did not develop in mice exposed to prolonged anti-angiogenic therapy using endostatin. Furthermore, repeated cycles of endostatin treatment in mice resulted in prolonged tumor dormancy and no recurrence of tumors following discontinuation of therapy (Boehm et al. (1997) Nature 390:404).

Despite promising results in mice, it has not been possible to produce clinical grade soluble, active angiostatin and endostatin in commercial quantities using *E. coli*, baculoviral, yeast, and mammalian expression systems. Expression in *E. coli* yielded insoluble protein aggregates of undefined composition, which could not be injected into humans. Other production methods, such as baculovirus and mammalian expression systems, yielded very low levels of the recombinant proteins (O'Reilly et al. (1997) Cell 88:277).

The poor yields of the expression systems to date may be explained by both angiostatin and endostatin being internal fragments of much larger proteins. The truncated proteins may not fold properly in the absence of the residues that are cleaved from the precursor molecules. For example, angiostatin has 26 cysteine residues which form numerous disulfide bonds. Expression of angiostatin by itself may not provide the optimal environment for these numerous disulfide bonds to form correctly in the secretory pathway. Also, the recombinant endostatin protein produced in *E. Coli* precipitated during dialysis, possibly due to the hydrophobicity of endostatin (O'Reilly et al. (1997) Cell 88:277).

A major hurdle with the use of angiostatin and endostatin in their present forms is that relatively large amounts of proteins have to be injected daily for weeks to months to achieve the desired clinical outcome. For example, in current mouse models, dosages of 20 mg/kg/day of endostatin are needed to demonstrate optimal efficacy (Boehm et al. (1997) Nature 390:404). Given that there is an urgent need to test endostatin and angiostatin clinically, a production method that can generate large quantities of clinical grade material is important.

One expression system that has been used to produce high level expression of fusion proteins in mammalian cells is a DNA construct encoding, a signal sequence, an immunoglobulin Fc region and a target protein. The fusion product of this construct generally is termed an "immunofusin." Several target proteins have been expressed successfully as immunofusins which include: IL2, CD26, Tat, Rev, OSF-2, βIG-H3, IgE Receptor, PSMA, and gp120. These expression constructs are disclosed in U.S. Pat. No. 5,541,087 and U.S. Pat. No. 5,726,044, the disclosures of which are incorporated herein by reference.

A major purpose of expressing recombinant fusion proteins in mammalian cells has been to attempt to confer novel or useful properties to the hybrid molecules, e.g., proper folding, increased solubility, targeting of a cytokine or toxin in vivo, Fc receptor binding, complement fixation, protein A binding, increased circulation half-life, and increased ability to cross the blood-brain barrier. Examples of recombinant fusion proteins produced in mammalian cells include cytokine immunoconjugates (Gillies et al. (1992) Proc. Natl. Acad. Sci. USA 89:1428; Gillies et al. (1993) Bioconjugate Chemistry 4:230), immunoadhesins (Capon et al. (1989) Nature 337:525), immunotoxins (Chaudhary et al. (1989) Nature 339:394), and a nerve growth factor conjugate (Friden et al. (1993) Science 259:373). Each of the foregoing publications is incorporated herein by reference.

It is an object of the invention to provide novel DNAs which facilitate efficient production and secretion of angiogenesis inhibitors in a variety of mammalian host cells. It is another object of the invention to provide methods for treating mammals with nucleic acids encoding, or amino acid sequences defining angiogenesis inhibitor proteins, including non-native, biosynthetic, or otherwise artificial proteins such as proteins which have been created by rational design.

SUMMARY OF THE INVENTION

The present invention features methods and compositions useful in making and using fusion proteins containing an angiogenesis inhibitor protein. The fusion proteins can facilitate a high level expression of biologically active angiogenesis inhibitor proteins. The angiogenesis inhibitor proteins can then be cleaved from the fusion protein and combined with a pharmaceutically acceptable carrier prior to administration to a mammal, for example, a human. Alternatively, nucleic sequences encoding, or amino acid sequences defining the angiogenesis inhibitor containing fusion proteins can be combined with a pharmaceutically acceptable carrier and administered to the mammal.

In one aspect, the invention provides nucleic acid molecules, for example, DNA or RNA molecules, encoding a fusion protein of the invention. The nucleic acid molecule encodes a signal sequence, an immunoglobulin Fc region, and at least one target protein, also referred to herein as the angiogenesis inhibitor protein, selected from the group consisting of angiostatin, endostatin, a plasminogen fragment having angiostatin activity, a collagen XVIII fragment having endostatin activity, and combinations thereof. In a preferred embodiment, the nucleic acid molecule encodes, serially in a 5' to 3' direction, the signal sequence, the immunoglobulin Fc region and the target protein sequence. In another preferred embodiment, the nucleic acid molecule encodes, serially in a 5' to 3' direction, the signal sequence, the target sequence, and immunoglobulin Fc region.

In another preferred embodiment, the immunoglobulin Fc region comprises an immunoglobulin hinge region and preferably comprises at least one immunoglobulin constant heavy region, for example, an immunoglobulin constant heavy 2 ($CH_2$) domain, an immunoglobulin constant heavy 3 ($CH_3$) domain), and depending upon the type of immunoglobulin used to generate the Fc region, optionally an immunoglobulin constant heavy region 4 (CH4) domain. In a more preferred embodiment, the immunoglobulin Fc region comprises a hinge region, a $CH_2$ domain and a $CH_3$ domain. Under certain circumstances, the immunoglobulin Fc region preferably lacks at least the $CH_1$ domain. Although the immunoglobulin Fc regions may be based on any immunoglobulin class, for example, IgA, IgD, IgE, IgG, and IgM, immunoglobulin Fc regions based on IgG are preferred.

In another embodiment, the nucleic acid of the invention can be incorporated in operative association into a replicable expression vector which can then be transfected into a mammalian host cell. In another preferred embodiment, the invention provides host cells harboring such nucleic acid sequences of the invention.

In another aspect, the invention provides a fusion protein comprising an immunoglobulin Fc region linked, either directly through a polypeptide bond or by means of a polypeptide linker, to a target protein selected from the group consisting of angiostatin, endostatin, a plasminogen fragment having angiostatin activity, a collagen XVIII fragment having endostatin activity, and combinations thereof. The target protein may be fused via its C-terminal end to an N-terminal end of the immunoglobulin Fc region. However, in a more preferred embodiment the target protein is fused via its N-terminal end to a C-terminal end of the immunoglobulin Fc region.

In another embodiment, the fusion protein may comprise a second target protein selected from the group consisting of angiostatin, endostatin, a plasminogen fragment having angiostatin activity, and a collagen XVIII fragment having endostatin activity. In this type of construct the first and second target proteins can be the same or different proteins. For example, in a preferred embodiment, the fusion protein comprises a first target protein of angiostatin, an immunoglobulin Fc region and a second target protein of endostatin. The first and second target proteins may be linked together, either directly or by means of a polypeptide linker. Alternatively, both target proteins may be linked, either directly or via a polypeptide linker, to the immunoglobulin Fc region. In the latter case, the first target protein is connected to an N-terminal end of the immunoglobulin Fc region and the second target protein is connected to a C-terminal end of the immunoglobulin Fc region.

In another embodiment, two fusion proteins may associate, either covalently, for example, by a disulfide or peptide bond, or non-covalently, to produce a multimeric protein. In a preferred embodiment, two fusion proteins are associated covalently by means of one or more disulfide bonds through cysteine residues, preferably located within immunoglobulin hinge regions disposed within the immunoglobulin Fc regions of both chains.

In a preferred embodiment, the target protein comprises a plasminogen fragment having a molecular weight of approximately 40 kD and, optionally comprises, an amino acid sequence as set forth in SEQ ID NO: 3. In another preferred embodiment, the target protein comprises a collagen XVIII fragment having an amino acid sequence set forth in SEQ ID NO: 1. Furthermore, the target protein can be full-length angiostatin or endostatin or bioactive fragments thereof. The source of the target protein in generating certain fusion proteins will depend upon the intended use of the target protein. For example, if the target protein is to be administered to a human, the target protein preferably is of human origin.

In another aspect, the invention provides methods of producing a fusion protein comprising an immunoglobulin Fc region and a target protein selected from the group consisting of angiostatin, endostatin, a plasminogen fragment having angiostatin activity, and a collagen XVIII fragment having endostatin activity. The method comprises the steps of (a) providing a mammalian cell containing a DNA molecule encoding such a fusion protein, either with or without a signal sequence, and (b) culturing the mammalian cell to produce the fusion protein. The resulting fusion protein can then be harvested, refolded, if necessary, and purified using conventional purification techniques well known and used in the art. Assuming that the fusion protein comprises a proteolytic cleavage site disposed between the immunoglobulin Fc region and the target protein, the target can be cleaved from the fusion protein using conventional proteolytic enzymes and if necessary, purified prior to use.

In another aspect, the invention provides methods for treating mammals, for example, a human, in need of an angiogenesis inhibitor based therapy. For example, it is contemplated that the angiogenesis inhibitors of the invention may be administered to a human afflicted with a tumor. Treatment with the angiogenesis inhibitor may slow down or stop tumor growth and, under certain circumstances, may cause tumor regression. Treatment may include administering to the mammal an amount of the angiogenesis inhibitor in an amount sufficient to slow down or stop tumor growth. The angiogenesis inhibitor may be provided in the form of a fusion protein or as a nucleic acid, preferably operatively associated with an expression vector, in combination with a pharmaceutically acceptable carrier.

The foregoing and other objects, features and advantages of the present invention will be made more apparent from the detailed description, drawings, and claims that follow.

BRIEF DESCRIPTION OF THE DRAWINGS

FIG. 1B, Fc-inner Kringle 1 of Angiostatin; FIG. 1C, Fc-Endostatin-GlySer linker-inner Kringle 1 of Angiostatin; FIG. 1D, Fc-Endostatin-GlySer linker-Kringle 1 of Angiostatin; FIG. 1E, Fc-Endostatin-GlySer linker-Angiostatin; FIG. 1F, Angiostatin-Fc-Endostatin. The vertical lines represent optional disulfide bonds connecting cysteine residues (C) disposal within a hinge region of the Fc molecule.

DETAILED DESCRIPTION OF THE INVENTION

Figure 1A:
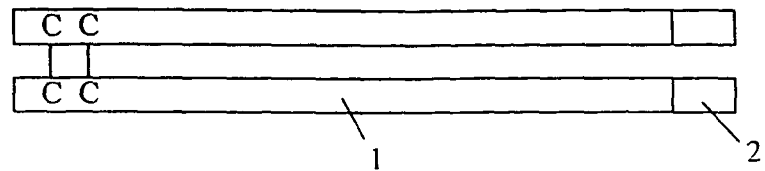
FIGS. 1A-1F are schematic illustrations of exemplary angiogenesis inhibitor fusion proteins constructed in accordance with the invention (see Examples 10-15). The Figures depict, respectively, FIG. 1A, Fc-Kringle 1 of Angiostatin.

The invention provides fusion proteins, referred to herein as immunofusins, which were useful in the production of commercial quantities of clinical grade angiogenesis inhibitors. The angiogenesis inhibitors may be cleaved from the immunofusin protein constructs prior to use. However, it is contemplated that the immunofusins or nucleic acids encoding the immunofusins may be administered directly to mammals in need of treatment with an angiogenesis inhibitor.

The invention thus provides fusion proteins comprising an immunoglobulin Fc region and at least one target protein, referred to herein as an angiogenesis inhibitor. The angiogenesis inhibitor preferably is selected from the group consisting of angiostatin, endostatin, a plasminogen fragment angiostatin activity, a collagen XVIII fragment having endostatin activity. It is contemplated, however, that other polypeptides having angiogenesis inhibitor activity, now known or late discovered, may be expressed as fusion proteins of the type described herein.

Six exemplary embodiments of protein constructs embodying the invention are illustrated in the drawing as FIGS. 1A-1F. Because dimeric constructs are preferred, all are illustrated as dimers cross-linked by a pair of disulfide bonds between cysteines on adjacent subunits. In the drawings, the disulfide bridges are depicted as linking together the portions of two immunoglobulin Fc regions via an immunoglobulin hinge region, and thus are characteristic of native forms of these molecules. While constructs including the hinge region of Fc are preferred and have been shown promise as therapeutic agents, the invention contemplates that the crosslinking at other positions may be chosen as desired. Furthermore, under some circumstances, dimers or multimers useful in the practice of the invention may be produced by non-covalent association, for example, by hydrophobic interaction.

Because homodimeric constructs are important embodiments of the invention, FIG. 1 illustrates such constructs. It should be appreciated that heterodimeric structures also are useful but, as is known to those skilled in the art, often can be difficult to purify. However, viable constructs useful to inhibit angiogenesis in various mammalian species, including humans, can be constructed comprising a mixture of homodimers and heterodimers. For example, one chain of the heterodimeric structure may comprise endostatin and the another may comprise angiostatin.

Figure 1B:
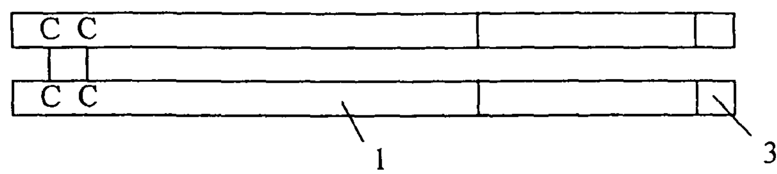
Figure 1C:
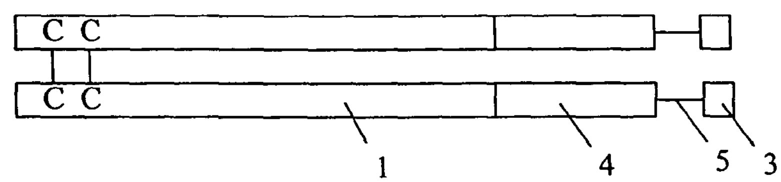
Figure 1D:
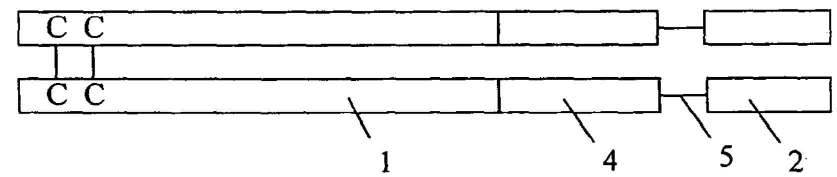
Figure 1E:
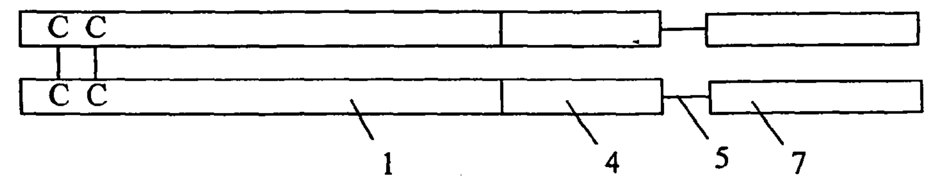

FIG. 1A illustrates a dimer construct produced in accordance with the procedure set forth in Example 10. Each monomer of the dimer comprises an immunoglobulin Fc region 1 including a hinge region, a $CH_2$ domain and a $CH_3$ domain. Attached directly to the C terminus of the Fc region 1 is the first Kringle region of angiostatin 2, both inner and outer rings. FIG. 1B shows a second embodiment of the invention (see Example 11) comprising the same Fc region as in FIG. 1A, this time having only the inner ring of Kringle one of angiostatin 3 attached to the C terminal end of the Fc region 1. FIGS. 1C through 1E depict various embodiments of the protein constructs of the invention, which include as a target protein plural angiogenesis inhibitors arranged in tandem and connected by a linker. In FIG. 1C, the target protein comprises full-length endostatin 4, a polypeptide linker 5, and the inner ring of Kringle one of angiostatin 3. FIG. 1D depicts a protein comprising an Fc region the same as that of FIG. 1A and a target protein comprising a full-length endostatin 4, a polypeptide linker 5, and a full Kringle one region of angiostatin (both inner and outer rings) 2. FIG. 1E differs from the construct of FIG. 1D in that the most C terminal protein domain comprises a full-length copy of angiostatin 7.

Figure 1F:
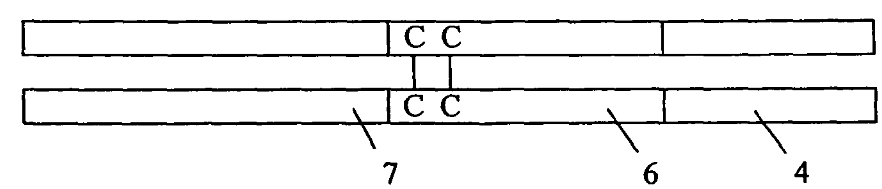

Although FIGS. 1A-1E represent Fc-X type constructs, where X is the target protein, it is contemplated that X-Fc type constructs may also be useful in the practice of the invention. Furthermore, it is contemplated the useful proteins of the invention may also be depicted by the formula X-Fc-X, wherein the Xs may represent the same or different target proteins. FIG. 1F depicts such a construct which comprises in an N- to C-terminal direction, full-length human angiostatin 7, a human immunoglobulin Fc region 6 including a hinge region, and full-length human endostatin domain 4.

The term "angiogenesis inhibitor," as used herein, refers to any polypeptide chain that reduces or inhibits the formation of new blood vessels in a mammal. With regard to cancer therapy, the angiogenesis inhibitor reduces or inhibits the formation of new blood vessels in or on a tumor, preferably in or on a solid tumor. It is contemplated that useful angiogenesis inhibitors may be identified using a variety of assays well known and used in the art. Such assays include, for example, the bovine capillary endothelial cell proliferation assay, the chick chorioallantoic membrane (CAM) assay or the mouse corneal assay. However, the CAM assay is preferred (see, for example, O'Reilly et al. (1994) Cell 79: 315-328 and O'Reilly et al. (1997) Cell 88: 277-285, the disclosures of which are incorporated herein by reference). Briefly, embryos with intact yolks are removed from fertilized three day old white eggs and placed in a petri dish. After incubation at 37° C., 3% $CO_2$ for three days, a methylcellulose disk containing the putative angiogenesis inhibitor is applied to the chorioallantoic membrane of an individual embryo. After incubation for about 48 hours, the chorioallantoic membranes were observed under a microscope for evidence of zones of inhibition.

Preferred angiogenesis inhibitors useful in the practice of the invention include, for example, angiostatin (O'Reilly et al. (1994) Cell 79: 315-328, and U.S. Pat. Nos. 5,733,876; 5,837,682; and 5,885,795), and endostatin (O'Reilly et al. (1997) Cell 88: 277-285 and U.S. Pat. No. 5,854,205). As stated previously, angiostatin and endostatin are specific inhibitors of endothelial cell proliferation and are capable of inhibiting tumor growth by blocking angiogenesis, the formation of new blood vessels that nourish tumors.

Angiostatin has been identified as a proteolytic fragment of plasminogen (O'Reilly et al. (1994) Cell 79: 315-328, and U.S. Pat. Nos. 5,733,876; 5,837,682; and 5,885,795, the disclosure of which is incorporated herein by reference). Specifically, angiostatin is a 38 kDa internal fragment of plasminogen containing at least three of the Kringle regions of plasminogen. Endostatin has been identified as a proteolytic fragment of collagen XVIII (O'Reilly et al. (1997) Cell 88: 277-285, the disclosure of which is incorporated herein by reference). Specifically, endostatin is a 20 kDa C-terminal fragment of collagen XVIII. The terms "angiostatin" and "endostatin," as used herein, refer not only to the full length proteins, but also to variants and bioactive fragments thereof, as well as to bioactive fragments of plasminogen and collagen XVIII, respectively. The term bioactive fragment, with respect to angiostatin refers to any protein fragment of plasminogen or angiostatin that has at least 30%, more preferably at least 70%, and most preferably at least 90% of the activity of full-length angiostatin as determined by the CAM assay. The term bioactive fragment, with respect to endostatin refers to any protein fragment of collagen XVIII or endostatin that has at least 30%, more preferably at least 70% and most preferably at least 90% of the activity of full length endostatin as determined by the CAM assay.

The term variants includes specifies and allelic variants, as well as other naturally occurring or non-naturally occurring variants, for example, generated by conventional genetic engineering protocols, that are at least 70% similar or 60% identical, more preferably at least 75% similar or 65% identical, and most preferably 80% similar or 70% identical to either the naturally-occurring sequences of endostatin or angiostatin disclosed herein.

To determine whether a candidate polypeptide has the requisite percentage similarity or identity to a reference polypeptide, the candidate amino acid sequence and the reference amino acid sequence are first aligned using the dynamic programming algorithm described in Smith and Waterman (1981), J. Mol. Biol. 147:195-197, in combination with the BLOSUM62 substitution matrix described in FIG. 2 of Henikoff and Henikoff (1992), "Amino acid substitution matrices from protein blocks", Proc. Natl. Acad Sci. USA 89:10915-10919. For the present invention, an appropriate value for the gap insertion penalty is −12, and an appropriate value for the gap extension penalty is −4. Computer programs performing alignments using the algorithm of Smith-Waterman and the BLOSUM62 matrix, such as the GCG program suite (Oxford Molecular Group, Oxford, England), are commercially available and widely used by those skilled in the art.

Once the alignment between the candidate and reference sequence is made, a percent similarity score may be calculated. The individual amino acids of each sequence are compared sequentially according to their similarity to each other. If the value in the BLOSUM62 matrix corresponding to the two aligned amino acids is zero or a negative number, the pair-wise similarity score is zero; otherwise the pair-wise similarity score is 1.0. The raw similarity score is the sum of the pair-wise similarity scores of the aligned amino acids. The raw score then is normalized by dividing it by the number of amino acids in the smaller of the candidate or reference sequences. The normalized raw score is the percent similarity. Alternatively, to calculate a percent identity, the aligned amino acids of each sequence again are compared sequentially. If the amino acids are non-identical, the pair-wise identity score is zero; otherwise the pair-wise identity score is 1.0. The raw identity score is the sum of the identical aligned amino acids. The raw score is then normalized by dividing it by the number of amino acids in the smaller of the candidate or reference sequences. The normalized raw score is the percent identity. Insertions and deletions are ignored for the purposes of calculating percent similarity and identity. Accordingly, gap penalties are not used in this calculation, although they are used in the initial alignment.

The target proteins disclosed herein are expressed as fusion proteins with an Fc region of an immunoglobulin. As is known, each immunoglobulin heavy chain constant region is comprised of four or five domains. The domains are named sequentially as follows: $CH_1$-hinge-$CH_2$—$CH_3$(—$CH_4$). The DNA sequences of the heavy chain domains have cross-homology among the immunoglobulin classes, e.g., the $CH_2$ domain of IgG is homologous to the $CH_2$ domain of IgA and IgD, and to the $CH_3$ domain of IgM and IgE.

As used herein, the term, "immunoglobulin Fc region" is understood to mean the carboxyl-terminal portion of an immunoglobulin chain constant region, preferably an immunoglobulin heavy chain constant region, or a portion thereof. For example, an immunoglobulin Fc region may comprise 1) a $CH_1$ domain, a $CH_2$ domain, and a $CH_3$ domain, 2) a $CH_1$ domain and a $CH_2$ domain, 3) a $CH_1$ domain and a $CH_3$ domain, 4) a $CH_2$ domain and a $CH_3$ domain, or 5) a combination of two or more domains and an immunoglobulin hinge region. In a preferred embodiment the Fc region used in the DNA construct includes at least an immunoglobulin hinge region a $CH_2$ domain and a $CH_3$ domain and preferably lacks at least the $CH_1$ domain.

The currently preferred class of immunoglobulin from which the heavy chain constant region is derived is IgG (Igγ) (γ subclasses 1, 2, 3, or 4). Other classes of immunoglobulin, IgA (Igα), IgD (Igδ), IgE (Igε) and IgM (Igμ), may be used. The choice of appropriate immunoglobulin heavy chain constant regions is discussed in detail in U.S. Pat. Nos. 5,541,087, and 5,726,044. The choice of particular immunoglobulin heavy chain constant region sequences from certain immunoglobulin classes and subclasses to achieve a particular result is considered to be within the level of skill in the art. The portion of the DNA construct encoding the immunoglobulin Fc region preferably comprises at least a portion of a hinge domain, and preferably at least a portion of a $CH_3$ domain of Fcγ or the homologous domains in any of IgA, IgD, IgE, or IgM.

Depending on the application, constant region genes from species other than human e.g., mouse or rat may be used. The Fc region used as a fusion partner in the immunofusin DNA construct generally may be from any mammalian species. Where it is undesirable to elicit an immune response in the host cell or animal against the Fc region, the Fc region may be derived from the same species as the host cell or animal. For example, human Fc can be used when the host animal or cell is human; likewise, murine Fc can be used where the host animal or cell will be a mouse. Further, substitution or deletion of constructs of these constant regions, in which one or more amino acid residues of the constant region domains are substituted or deleted also would be useful. One example would be to introduce amino acid substitutions in the upper $CH_2$ region to create a Fc variant with reduced affinity for Fc receptors (Cole et al. (1997) J. Immunol. 159:3613). One of ordinary skill in the art can prepare such constructs using well known molecular biology techniques.

The use of human Fcγ1 as the Fc region sequence has several advantages. For example, if the angiogenesis inhibitor Fc fusion protein is to be used as a biopharmaceutical, the Fcγ1 domain may confer the effector function activities to the fusion protein. The effector function activities include the biological activities such as complement fixation, antibody-directed cellular cytotoxicity, placental transfer, and increased serum half-life. The Fc domain also provides for detection by anti-Fc ELISA and purification through binding to *Staphylococcus aureus* protein A ("Protein A"). In certain applications, however, it may be desirable to delete specific effector functions from the Fc region, such as Fc receptor binding or complement fixation.

In the case of angiogenesis inhibitor immunofusins, one function of the immunoglobulin Fc fusion partner is to facilitate proper folding of the angiogenesis inhibitor protein to yield active angiogenesis inhibitor protein and to impact solubility to the active moieties, at least in the extracellular medium. Since the Fc fusion partner is hydrophilic, the angiogenesis inhibitor immunofusin readily is soluble unlike, for example, the recombinant endostatin produced in *E. coli* (O'Reilly (1997) Cell 88:277.) In all of the Examples disclosed herein, high levels of production of the immunofusins were obtained. The angiogenesis inhibitor immunofusins were secreted into media at concentrations typically of about 30 to 100 μg/ml, and could be purified readily to homogeneity by Protein A chromatography. In addition, the angiogenesis inhibitor immunofusins could be cleaved and further purified using conventional purification protocols using, for example, by heparin sepharose, lysine sepharose or affinity purification.

In addition to the high levels of expression, fusion proteins of the invention also exhibit longer serum half-lives, presumably due to their larger molecular sizes. For example, human Fc-human angiostatin has a serum half-life of 33 hours in mouse, as compared to 4-6 hours for human angiostatin (O'Reilly et al. (1996) Nature Medicine 2:689). It is believe that angiostatin with a molecular weight of 40 kD, and endostatin with a molecular weight of 20 kD, are small enough to be cleared efficiently by renal filtration. In contrast, the dimeric forms of Fc-angiostatin and dimeric Fc-endostatin are 145 kD and 100 kD, respectively, because there are two immunoglobulin Fc regions attached to either two angiostatin molecules or two endostatin molecules. Such a bivalent structure may exhibit a higher binding affinity to the angiostatin or endostatin receptor. If the angiogenesis inhibiting activity is receptor-mediated, the Fc fusion proteins are potentially more effective to suppress tumors than monovalent angiostatin or monovalent endostatin by themselves. Furthermore, if angiostatin and/or endostatin belong to a class of dimeric protein ligands, the physical constraint imposed by the Fc on angiostatin or endostatin would make the dimerization an intramolecular process, thus shifting the equilibrium in favor of the dimer and enhancing its binding to the receptor. Cysteine residues can also be introduced by standard recombinant DNA technology to the monomer at appropriate places to stabilize the dimer through covalent disulfide bond formation.

As used herein, the term "multivalent" refers to a recombinant molecule that incorporates two or more biologically active segments. The protein fragments forming the multivalent molecule may be linked through a polypeptide peptide linker which attaches the constituent parts without causing a frame shift and permits each to function independently.

As used herein, the term "bivalent" refers to a multivalent recombinant molecule having two target proteins in a fusion construct of the invention, e.g., an Fc-X molecule, where X independently is selected from angiostatin, endostatin, or a variant thereof. Since there are two X moieties fused to an immunoglobulin Fc region (which typically itself is a dimer of the heavy chain fragments including at least a portion of the hinge region and $CH_3$ domain, and optionally the $CH_2$ domain), the molecule is bivalent (see, e.g., FIG. 1A). If the fusion construct of the invention has the form Fc-X-X, the resulting Fc dimer molecule is tetravalent. The two proteins forming the Fc-X-X molecule may be linked through a peptide linker. A bivalent molecule can increase the apparent binding affinity between the molecule and its receptor. For instance, if one endostatin moiety of an Fc-endostatin can bind to a receptor on a cell with a certain affinity, the second endostatin moiety of the same Fc-endostatin may bind to a second receptor on the same cell with a much higher avidity (apparent affinity). This is because of the physical proximity of the second endostatin moiety to the receptor after the first endostatin moiety is already bound. In the case of an antibody binding to an antigen, the apparent affinity is increased by at least $10^4$.

As used herein, the terms "multimer" and "multimeric" refers to the stable association of two or more polypeptide chains either covalently, for example, by means of covalent interaction, for example, by a disulfide bond or non-covalently, for example, by hydrophobic interaction. The term multimer is intended to encompass both homomultimers, wherein the polypeptides are the same, as well as heteromultimers, wherein the polypeptides are different.

As used herein, the term "dimeric" refers to a specific multimeric molecule where two protein polypeptide chains are stably associated through covalent or non-covalent interactions. It should be understood that the immunoglobulin Fc region Fc fragment itself typically is a dimer of the heavy chain fragments including at least a portion of the hinge region and $CH_3$ domain, and optionally the $CH_2$ domain. Many protein ligands are known to bind to their receptors as a dimer. If a protein ligand X dimerizes naturally, the X moiety in an Fc-X molecule will dimerize to a much greater extent, since the dimerization process is concentration dependent. The physical proximity of the two X moieties connected by associated immunoglobulin Fc region would make the dimerization an intramolecular process, greatly shifting the equilibrium in favor of the dimer and enhancing its binding to the receptor.

It is understood that the present invention exploits conventional recombinant DNA methodologies for generating the Fc fusion proteins useful in the practice of the invention. The Fc fusion constructs preferably are generated at the DNA level, and the resulting DNAs integrated into expression vectors, and expressed to produce the immunofusins. As used herein, the term "vector" is understood to mean any nucleic acid comprising a nucleotide sequence competent to be incorporated into a host cell and to be recombined with and integrated into the host cell genome, or to replicate autonomously as an episome. Such vectors include linear nucleic acids, plasmids, phagemids, cosmids, RNA vectors, viral vectors and the like. Non-limiting examples of a viral vector include a retrovirus, an adenovirus and an adeno-associated virus. As used herein, the term "gene expression" or "expression" of a target protein, is understood to mean the transcription of a DNA sequence, translation of the mRNA transcript, and secretion of an Fc fusion protein product.

A useful expression vector is pdCs (Lo et al. (1988) Protein Engineering 11:495, the disclosure of which is incorporated herein by reference) in which the transcription of the Fc-X gene utilizes the enhancer/promoter of the human cytomegalovirus and the SV40 polyadenylation signal. The enhancer and promoter sequence of the human cytomegalovirus used was derived from nucleotides −601 to +7 of the sequence provided in Boshart et al., 1985, Cell 41:521, the disclosure of which is incorporated herein by reference. The vector also contains the mutant dihydrofolate reductase gene as a selection marker (Simonsen and Levinson (1983) Proc. Nat. Acad. Sci. USA 80:2495, the disclosure of which is incorporated herein by reference).

An appropriate host cell can be transformed or transfected with the DNA sequence of the invention, and utilized for the expression and secretion of a target protein. Currently preferred host cells for use in the invention include immortal hybridoma cells, NS/O myeloma cells, 293 cells, Chinese hamster ovary cells, Hela cells, and COS cells.

The fusion proteins of the invention preferably are generated by conventional recombinant DNA methodologies. The fusion proteins preferably are produced by expression in a host cell of a DNA molecule encoding a signal sequence, an immunoglobulin Fc region and a target protein (also referred to herein as an angiogenesis inhibitor). Preferred constructs may encode in a 5' to 3' direction, the signal sequence, the immunoglobulin Fc region and the target protein. Alternatively, the constructs may encode in a 5' to 3' direction, the signal sequence, the target protein and the immunoglobulin Fc region.

As used herein, the term "signal sequence" is understood to mean a peptide segment which directs the secretion of the angiogenesis inhibitor immunofusin protein and is thereafter cleaved following translation in the host cell. The signal sequence of the invention is a polynucleotide, which encodes an amino acid sequence that initiates transport of a protein across the membrane of the endoplasmic reticulum. Signal sequences which will be useful in the invention include antibody light chain signal sequences, e.g., antibody 14.18 (Gillies et. al., 1989, Jour. of Immunol. Meth., 125:191-202), antibody heavy chain signal sequences, e.g., the MOPC141 antibody heavy chain signal sequence (Sakano et al., 1980, Nature 286:5774), and any other signal sequences which are known in the art (see for example, Watson, 1984, Nucleic Acids Research 12:5145). Each of these references is incorporated herein by reference.

Signal sequences have been well characterized in the art and are known typically to contain 16 to 30 amino acid residues, and may contain greater or fewer amino acid residues. A typical signal peptide consists of three regions: a basic N-terminal region, a central hydrophobic region, and a more polar C-terminal region. The central hydrophobic region contains 4 to 12 hydrophobic residues that anchor the signal peptide across the membrane lipid bilayer during transport of the nascent polypeptide. Following initiation, the signal peptide is usually cleaved within the lumen of the endoplasmic reticulum by cellular enzymes known as signal peptidases. Potential cleavage sites of the signal peptide generally follow the "(−3, −1) rule." Thus a typical signal peptide has small, neutral amino acid residues in positions −1 and −3 and lacks proline residues in this region. The signal peptidase will cleave such a signal peptide between the −1 and +1 amino acids. Thus, the portion of the DNA encoding the signal sequence may be cleaved from the amino-terminus of the immunofusin protein during secretion. This results in the secretion of a immunofusin protein consisting of the Fc region and the target protein. A detailed discussion of signal peptide sequences is provided by von Heijne (1986) Nucleic Acids Res., 14:4683 the disclosure of which is incorporated herein by reference.

As would be apparent to one of skill in the art, the suitability of a particular signal sequence for use in the invention may require some routine experimentation. Such experimentation will include determining the ability of the signal sequence to direct the secretion of an immunofusin and also a determination of the optimal configuration, genomic or cDNA, of the sequence to be used in order to achieve efficient secretion of immunofusins. Additionally, one skilled in the art is capable of creating a synthetic signal peptide following the rules presented by von Heijne, referenced above, and testing for the efficacy of such a synthetic signal sequence by routine experimentation. A signal sequence may also be referred to as a "signal peptide," "leader sequence," or "leader peptide."

The fusion of the signal sequence and the immunoglobulin Fc region is sometimes referred to herein as secretion cassette. An exemplary secretion cassette useful in the practice of the invention is a polynucleotide encoding, in a 5' to 3' direction, a signal sequence of an immunoglobulin light chain gene and an Fcγ1 region of the human immunoglobulin γ1 gene. The Fcγ1 region of the immunoglobulin Fcγ1 gene preferably includes at least a portion of the hinge domain and at least a portion of the $CH_3$ domain, or alternatively at least portions of the hinge domain, $CH_2$ domain and $CH_3$ domain. The DNA encoding the secretion cassette can be in its genomic configuration or its cDNA configuration.

In another embodiment, the DNA sequence encodes a proteolytic cleavage site interposed between the secretion cassette and the angiogenesis inhibitor protein. A cleavage site provides for the proteolytic cleavage of the encoded fusion protein thus separating the Fc domain from the angiogenesis inhibitor protein. As used herein, "proteolytic cleavage site" is understood to mean amino acid sequences which are preferentially cleaved by a proteolytic enzyme or other proteolytic cleavage agents. Useful proteolytic cleavage sites include amino acids sequences which are recognized by proteolytic enzymes such as trypsin, plasmin or enterokinase K. Many cleavage site/cleavage agent pairs are known. See, for example, U.S. Pat. No. 5,726,044, the disclosure of which is incorporated herein by reference. Where the target protein sequence is a precursor molecule to angiostatin, endostatin, or an active variant thereof, the desired protein product may be produced by cleavage with the endogenous proteolytic enzyme, such as elastin or plasmin or urokinase.

The present invention also encompasses fusion proteins containing different combinations of recombinant angiostatin and endostatin, or fragments thereof, which can be made in large quantities. Despite the demonstrated efficacy in suppressing tumor growth, the mechanism of how angiostatin and endostatin block angiogenesis is not completely known. Angiostatin has several Kringle structures and endostatin has different structural motifs, each of which may be solely responsible for or assist in binding of the proteins to endothelial cells and exerting an anti-angiogenic effect. Accordingly, this invention includes target proteins which are bioactive fragments of angiostatin, such as Kringle 1, Kringle 2, Kringle 3, and combinations thereof, and endostatin which exhibit physiologically similar behavior to naturally occurring full-length angiostatin and endostatin.

Another embodiment of the present invention provides for bifunctional hybrid constructs of angiogenesis inhibitors. As used herein, a bifunctional hybrid molecule or construct means a protein produced by combining two protein subunits, where the two subunits can be derived from different proteins. Each protein subunit has its own independent function so that in the hybrid molecule, the functions of the two subunits may be additive or synergistic. Such functional hybrid proteins would allow the synergistic effect of angiostatin and endostatin to be explored in animal models. A preferred bifunctional hybrid may comprise at least two different angiogenesis inhibitors linked in tandem, either directly or by means of a polypeptide linker. For example, in a preferred embodiment, the target sequence encodes at least a portion of angiostatin linked in frame with at least a portion of endostatin and both the angiostatin and endostatin domains exhibit anti angiogenesis activity or angiogenesis inhibition. The two units may be linked by a polypeptide linker.

As used herein the term "polypeptide linker is understood to mean an peptide sequence that can link two proteins together or a protein and an Fc region. The polypeptide linker preferably comprises a plurality of amino acids such as glycine and/or serine. Preferably, the polypeptide linker comprises a series of glycine and serine peptides about 10-15 residues in length. See, for example, U.S. Pat. No. 5,258,698, the disclosure of which is incorporated herein by reference. It is contemplated however, that the optimal linker length and amino acid composition may be determined by routine experimentation.

It is found that when different parts of the angiostatin are expressed as Fc fusion molecules, high levels of expression are obtained, presumably because the Fc portion acts as a carrier, helping the polypeptide at the C-terminus to fold correctly. In addition, the Fc region can be glycosylated and highly charged at physiological pH, thus the Fc region can help to solubilize hydrophobic proteins.

The present invention also provides methods for the production of angiostatin and endostatin of non-human species as Fc fusion proteins. Non-human angiogenesis inhibitor fusion proteins are useful for preclinical studies of angiogenesis inhibitors because efficacy and toxicity studies of a protein drug must be performed in animal model systems before testing in humans. A human protein may not work in a mouse model because the protein may elicit an immune response, and/or exhibit different pharmacokinentics skewing the test results. Therefore, the equivalent mouse protein is the best surrogate for the human protein for testing in a mouse model.

The standard Lewis lung carcinoma model in mice (O'Reilly et al. (1997) Cell 88:277) was used to compare soluble huFc-huAngiostatin, huFc-huEndostatin, muFc-muAngiostatin, muFc-muEndostatin with the insoluble proteins produced in an *E. coli* expression system. The soluble Fc fusion proteins were more efficacious in suppressing tumor growth in the Lewis lung model than the corresponding proteins produced in *E. coli*. Furthermore, laboratory mice are inbred and their tumors are induced and not spontaneous. Therefore, efficacy in a mouse model may not correlate to probable efficacy against human tumors. Preclinical studies in dogs will provide more precise information about the efficacy of these angiogenesis inhibitors on spontaneous tumors because there are numerous naturally occurring, spontaneous canine tumors. The methods of producing murine (mu) Fc-mu angiostatin, muFc-mu endostatin, and canine (ca) Fc-ca angiostatin, caFc-ca endostatin of the present invention will facilitate preclinical studies of angiogenesis inhibitors in both murine and canine systems.

The present invention provides methods of treating a condition mediated by angiogenesis by administering the DNA, RNA or proteins of the invention. Conditions mediated by angiogenesis include, for example: solid tumors; blood born tumors, tumor metastasis, benign tumors including hemangiomas, acoustic neuromas, neurofibromas, trachomas, and pyrogenic granulomas; rheumatoid arthritis; psoriasis; ocular angiogenic diseases (diabetic retinopathy, retinopathy of prematurity, macular degeneration, corneal graft rejection, neovascular glaucoma) retrolental fibroplasia, rubeosis, Osler-Webber Syndrome; myocardial angiogenesis; plaque neovascularization; telangiectasia; hemophiliac joints' angiofibroma; and wound granulation; and excessive or abnormal stimulation of endothelial cells, intestinal adhesions, artherosclerosis, sclerodermal and hypertrophic scars, i.e., keloids.

The DNA constructs disclosed herein can be useful in gene therapy procedures in which the endostatin or angiostatin gene is delivered into a cell by one of various means e.g., native DNA associated with a promoter or DNA within a viral vector. Once inside a cell, the angiostatin and/or endostatin gene or gene fragment is expressed and the protein is produced in vivo to carry out its normal biological function. The DNA construct of the present invention results in high levels of expression of the fusion protein. The fusion proteins of the present invention may also be useful in treating conditions mediated by angiogenesis and may have greater clinical efficacy than native angiogenesis inhibitors and other recombinant angiogenesis inhibitors because the angiogenesis inhibitor immunofusins of the present invention have a longer serum half-life than the other recombinant angiogenesis inhibitors or native angiogenesis inhibitors alone. The bivalent and dimeric forms of the present invention should have higher binding affinity due to the bivalent and dimeric structure. The bifunctional hybrid molecules of the present invention may have a higher clinical efficacy due to possible synergistic effects of two different angiogenesis inhibitors connected by the fused Fc region or a flexible polypeptide linker.

The compositions of the present invention may be provided to an animal by any suitable means, directly (e.g., locally, as by injection, implantation or topical administration to a tissue locus) or systemically (e.g., parenterally or orally). Where the composition is to be provided parenterally, such as by intravenous, subcutaneous, ophthalmic, intraperitoneal, intramuscular, buccal, rectal, vaginal, intraorbital, intracerebral, intracranial, intraspinal, intraventricular, intrathecal, intracisternal, intracapsular, intranasal or by aerosol administration, the composition preferably comprises part of an aqueous or physiologically compatible fluid suspension or solution. Thus, the carrier or vehicle is physiologically acceptable so that in addition to delivery of the desired composition to the patient, it does not otherwise adversely affect the patient's electrolyte and/or volume balance. The fluid medium for the agent thus can comprise normal physiologic saline (e.g., 9.85% aqueous NaCl, 0.15 M, pH 7-7.4).

Preferred dosages of the immunofusins per administration are within the range of 50 ng/$m^2$ to 1 g/$m^2$, more preferably 5 μg/$m^2$ to 200 mg/$m^2$, and most preferably 0.1 mg/$m^2$ to 50 mg/$m^2$. Preferred dosages of nucleic acids encoding the immunofusins per administration are within the range of 1 μg/$m^2$ to 100 mg/$m^2$, more preferably 20 μg/$m^2$ to 10 mg/$m^2$, and most preferably 400 μg/$m^2$ to 4 mg/$m^2$. It is contemplated, however, that the optimal modes of administration, and dosages may be determined by routine experimentation well within the level of skill in the art.

The invention is illustrated further by the following non-limiting examples.

EXAMPLES

Example 1

Expression of huFc-huEndostatin

Human endostatin was expressed as a human Fc-human endostatin (huFc-huEndo) fusion protein according to the teachings of Lo et al. (1998) Protein Engineering 11:495. Fc refers to the Fc fragment of the human immunoglobulin gamma (DNA sequence set forth in SEQ ID NO:1; amino acid sequence set forth in SEQ ID NO:2). (Polymerase chain reactions PCR) was used to adapt the endostatin cDNA (SEQ ID NO:3; whose amino acid sequence is disclosed in SEQ ID NO:4), for expression in an Fc-Endo fusion protein. The forward primer was either 5'-CC CCG GGT AAA CAC AGC CAC CGC GAC TTC C (SEQ ID NO:5; encoded amino acids disclosed in SEQ ID NO:6) or 5'-C AAG CTT CAC AGC CAC CGC GAC TTC C (SEQ ID NO:7; encoded amino acids disclosed in SEQ ID NO:8), where the XmaI site or the HindIII site was followed by sequence encoding the N-terminus of endostatin. The primer with the XmaI site adapted the endostatin cDNA for ligation to the XmaI site at the end of the $CH_3$ domain of the IgGFc region. The primer with the HindIII site adapted the endostatin cDNA for ligation to the HindIII site of the pdCs-Fc($D_4$K) vector, which contains the enterokinase recognition site $Asp_4$-Lys (LaVallie et al. (1993) J. Biol. Chem. 268:23311-23317) at the junction of the fusion protein. The reverse primer was 5'-C CTC GAG CTA CTT GGA GGC AGT CAT G (SEQ ID NO:9), which was designed to put a translation STOP codon (anticodon, CTA) immediately after the C-terminus of endostatin, and this was followed by an XhoI site. The PCR products were cloned and sequenced, and the XmaI-XhoI fragment was ligated to the resulting XmaI and XhoI digested pdCs-Fc vector. Similarly, the HindIII-XhoI fragment encoding endostatin was ligated into appropriately digested pdCs-huFc($D_4$K) vector. Stable clones expressing Fc-endo or Fc($D_4$K)-endostatin were obtained by electroporation of NS/0 cells followed by selection in growth medium containing 100 nM methotrexate. Protein expression level was assayed by anti-human Fc ELISA (Example 3) and confirmed by SDS-PAGE, which showed a protein product of ~52 kD. The best producing clones were subcloned by limiting dilutions.

Example 2

Cell Culture and Transfection

For transient transfection, the plasmid was introduced into human kidney 293 cells by co-precipitation of plasmid DNA with calcium phosphate (Sambrook et al. (1989) Molecular Cloning—A Laboratory Manual, Cold Spring Harbor, N.Y.) or by lipofection using LipofectAMINE Plus (Life Technologies, Gaithersburg, Md.) according to supplier's protocol.

In order to obtain stably transfected clones, plasmid DNA was introduced into the mouse myeloma NS/0 cells by electroporation. NS/0 cells were grown in Dulbecco's modified Eagle's medium supplemented with 10% fetal bovine serum. About $5\times10^6$ cells were washed once with PBS and resuspended in 0.5 ml PBS. Ten μg of linearized plasmid DNA then was incubated with the cells in a Gene Pulser Cuvette (0.4 cm electrode gap, BioRad, Hercules, Calif.) on ice for 10 min. Electroporation was performed using a Gene Pulser (BioRad, Hercules, Calif.) with settings at 0.25 V and 500 μF. Cells were allowed to recover for 10 min. on ice, after which they were resuspended in growth medium and then plated onto two 96 well plates. Stably transfected clones were selected by growth in the presence of 100 nM methotrexate (MTX), which was introduced two days post-transfection. The cells were fed every 3 days for three more times, and MTX-resistant clones appeared in 2 to 3 weeks. Supernatants from clones were assayed by anti-Fc ELISA to identify high producers. High producing clones were isolated and propagated in growth medium containing 100 nM MTX.

Example 3

ELISA Procedures

Three different ELISAs were used to determine the concentrations of protein products in the supernatants of MTX-resistant clones and other test samples. The anti-human Fc (huFc) ELISA was used to measure the amount of human Fc-containing proteins. The anti-murine Fc (muFc) and anti-canine Fc (caFc) antibodies were used in ELISAs to measure the amount of murine Fc- and canineFc-containing proteins, respectively. The procedure for the anti-huFc ELISA is described in detail herein below.

A. Coating Plates

ELISA plates were coated with AffiniPure Goat anti-Human IgG (H+L) (Jackson ImmunoResearch Laboratories, West Grove, Pa.) at 5 μg/ml in PBS, and 100 μl/well in 96-well plates (Nunc-Immuno plate MaxiSorp™, Nalge Nunc International, Rochester, N.Y.). Coated plates were covered and incubated at 4° C. overnight. Plates then were washed 4 times with 0.05% Tween 20 in PBS, and blocked with 1% BSA/1% Goat Serum in PBS, 200 μl/well. After incubation with the blocking buffer at 37° C. for 2 hours, the plates were washed 4 times with 0.05% Tween in PBS and tapped dry on paper towels.

B. Incubation with Test Samples and Secondary Antibody

Test samples were diluted to the proper concentrations in a sample buffer, containing 1% BSA/1% Goat Serum/0.05% Tween in PBS. A standard curve was prepared with a chimeric antibody (with a human Fc), the concentration of which was known. To prepare a standard curve, serial dilutions were made in the sample buffer to give a standard curve ranging from 125 ng/ml to 3.9 ng/ml. The diluted samples and standards were added to the plate, 100 μl/well and the plate was then incubated at 37° C. for 2 hr. After incubation, the plate was washed 8 times with 0.05% Tween in PBS. To each well was then added 100 μl of secondary antibody, the horse radish peroxidase (HRP)-conjugated anti-human IgG (Jackson ImmunoResearch Laboratories, Inc. West Grove, Pa.), diluted about 1:120,000 in sample buffer. The exact dilution of the secondary antibody had to be determined for each lot of the HRP-conjugated Anti-Human IgG. After incubation at 37° C. for 2 hr, the plate was washed 8 times with 0.05% Tween in PBS.

C. Development

A substrate solution was prepared by dissolving 30 mg (1 tablet) of o-phenylenediamine dihydrochloride (OPD) into 15 ml of 0.025 M citric acid/0.05 M $Na_2HPO_4$ buffer, pH 5, containing 0.03% of freshly added $H_2O_2$. The substrate solution was added to the plate at 100 μl/well. The color was allowed to develop for 30 min. at room temperature in the dark. The developing time can be subject to change, depending on lot to lot variability of the coated plates, the secondary antibody, etc. The reaction was stopped by adding 4N $H_2SO_4$, 100 μl/well. The plate was read by a plate reader, which was set at both 490 and 650 nm, and programmed to subtract the background OD at 650 nm from the OD at 490 nm.

The procedure for the anti-muFc ELISA was similar, except that ELISA plate was coated with AffiniPure Goat anti-murine IgG (H+L) (Jackson ImmunoResearch, West Grove, Pa.) at 5 μg/ml in PBS, and 100 μl/well; and the secondary antibody was horse radish peroxidase-conjugated goat anti-muIgG, Fcγ (Jackson ImmunoResearch West Grove, Pa.), used at 1 in 5000 dilution. Similarly, for the anti-caFc ELISA, the ELISA plate was coated with AffiniPure Rabbit anti-dog IgG, Fc Fragment specific (Jackson ImmunoResearch, West Grove, Pa.) at 5 μg/ml in PBS, and 100 μl/well; and the secondary antibody was horse radish peroxidase-conjugated AffiniPure rabbit anti-dog IgG, Fc fragment specific (Jackson ImmunoResearch, West Grove, Pa.), used at 1 in 5000 dilution.

Example 4

Expression of huFc-huAngiostatin

Human angiostatin (DNA sequence set forth in SEQ ID NO:10; amino acid sequence set forth in SEQ ID NO:11) was expressed as a human Fc-human angiostatin (huFc-huAngio) fusion protein essentially as described in Example 1. PCR was used to adapt the angiostatin cDNA (SEQ ID NO:3), for expression in the pdCs-huFc or pdCs-huFc($D_4$K) vectors. The respective forward primers were 5'-CC CCG GG T AAG AAA GTG TAT CTC TCA GAG (SEQ ID NO 12; encoded amino acids disclosed in SEQ ID NO:13), and 5'-C CCC AAG CTT AAA GTG TAT CTC TCA GAG (SEQ ID NO:14; encoded amino acids disclosed in SEQ ID NO:15), where the XmaI site or the HindIII site was followed by sequence encoding the N-terminus of angiostatin. The reverse primer was 5'-CCC CTC GAG CTA CGC TTC TGT TCC TGA GCA (SEQ ID NO:16), which was designed to put a translation STOP codon (anticodon, CTA) immediately after the C-terminus of angiostatin, and this was followed by an XhoI site. The PCR products were cloned and sequenced, and the resulting XmaI-XhoI fragment and the HindIII-XhoI fragment encoding angiostatin were ligated to the pdCs-huFc and the pdCs-huFc($D_4K$) vectors, respectively. Stable NS/0 clones expressing huFc-huAngio and huFc($D_4K$)-huAngio were selected and assayed as described in Examples 2 and 3.

Example 5

Expression of muFc-mu-Endostatin

Murine endostatin (DNA sequence set forth in SEQ ID NO:17; amino acid sequence set forth in SEQ ID NO:18) and murine Fc (DNA sequence set forth in SEQ ID NO:19; encoded amino acids set forth in SEQ ID NO:20) were expressed as a murine Fc-murine endostatin (muFc-muEndo) fusion protein essentially as described in Example 1. PCR was used to adapt the endostatin cDNA (SEQ ID NO:4), for expression in the pdCs-muFc($D_4K$) vector. The forward primer was 5'-C CCC AAG CTT CAT ACT CAT CAG GAC TTT C (SEQ ID NO:21; encoded amino acids disclosed in SEQ ID NO:22), where the HindIII site was followed by sequence encoding the N-terminus of endostatin. The reverse primer was 5'-CCC CTC GAG CTA TTT GGA GAA AGA GGT C (SEQ ID NO:23), which was designed to put a translation STOP codon (anticodon, CTA) immediately after the C-terminus of endostatin, and this was followed by an XhoI site. The PCR product was cloned and sequenced, and the resulting HindIII-XhoI fragment encoding endostatin was ligated into the pdCs-muFc($D_4K$) vector. Stable NS/0 clones expressing muFc($D_4K$)-muEndo were selected and assayed (anti-muFc ELISA) as described in Examples 2 and 3.

Example 6

Expression of muFc-muAngiostatin

Murine angiostatin (DNA sequence set forth in SEQ ID NO:24; amino acid sequence set forth in SEQ ID NO:25) was expressed as a murine Fc-murine angiostatin (muFc-muAngio) fusion protein essentially as described in Example 1. PCR was used to adapt the angiostatin cDNA (SEQ ID NO:6) for expression in the pdCs-Fc($D_4K$) vector. The forward primer was 5'-C CCC AAG CTT GTG TAT CTG TCA GAA TGT AAG CCC TCC TGT CTC TGA GCA (SEQ ID NO: 26; encoded amino acids disclosed in SEQ ID NO:27), where the HindIII site was followed by sequence encoding the N-terminus of angiostatin. The reverse primer was 5'-CCC CTC GAG CTA CCC TCC TGT CTC TGA GCA (SEQ ID NO:28), which was designed to put a translation STOP codon (anticodon, CTA) immediately after the C-terminus of angiostatin, and this was followed by an XhoI site (CTCGAG). The PCR product was cloned and sequenced, and the HindIII-XhoI fragment encoding angiostatin was ligated to the pdCs-muFc ($D_4K$) vector. Stable NS/0 clones expressing muFc($D_4K$)-muAngio were selected and assayed (anti-muFc ELISA) as described in Examples 2 and 3.

Example 7

Expression of Canine Fc (caFc)

Canine peripheral blood monocytic cells (PBMCs) isolated from dog's blood were used to prepare mRNA. After synthesis of the first strand cDNA with reverse transcriptase and oligo(dT), PCR was performed to amplify the canine Fc (Kazuhiko et al., (1992) JP 1992040894-A1) using the forward primer 5'-CC TTA AGC GAA AAT GGA AGA GTT CCT CGC (SEQ ID NO:29; encoded amino acids disclosed in SEQ ID NO:30), in which an AflII site was introduced immediately upstream of the sequence encoding the hinge region of the canine Fc, and the reverse primer 5'-C CTC GAG TCA TTT ACC CGG GGA ATG GGA GAG GGA TTT CTG (SEQ ID NO:31), in which an XhoI site was introduced after the translation STOP codon (anticodon, TCA) of the canine Fc. The reverse primer also introduced a silent mutation to create a XmaI restriction site, which facilitates the construction of the pdCs-caFc($D_4K$) vector through a linker-adaptor and ligation to DNA constructs encoding canine endostatin or angiostatin. Similar to the construction of pdCs-huFc, which was described in detail in Lo et al. (Lo et al., Protein Engineering (1998) 11:495), the expression vector for the pdCs-caFc was constructed as follows. The AflII-XhoI fragment encoding the canine Fc was ligated to the XbaI-AflII fragment encoding the light chain signal peptide and the XbaI-XhoI digested pdCs vector. The resulting pdCs-caFc expression vector then was used to transfect 293 cells. About 3 days post-transfection, the supernatant was purified by Protein A chromatography. Expression of dog Fc (DNA sequence set forth in SEQ ID NO:32; amino acid sequence set forth in SEQ ID NO:33) was confirmed by SDS-PAGE followed by Western blot analysis using a peroxidase-conjugated Rabbit anti-Dog IgG, Fc fragment specific (Jackson ImmunoResearch, West Grove, Pa.).

Example 8

Expression of caFc-caEndostatin

The coding sequence for canine endostatin (DNA sequence set forth in SEQ ID NO:34; amino acid sequence set forth in SEQ ID NO:35) was adapted to a HindIII-XhoI fragment for expression as a Fc fusion protein, essentially as described in Example 5. At the 3' end, a STOP codon was introduced, for example, by PCR, immediately after the codon encoding the C-terminal lysine residue, and this was followed by the NotI restriction site. At the 5' end, however, there was a DraIII restriction site convenient for reconstruction. An oligonucleotide duplex consisting of a HindIII and a DraIII sticky ends was chemically synthesized and used to ligate to the DraIII-XhoI restriction fragment which encodes the rest of the canine endostatin cDNA. The duplex used is shown below:

```
HindIII
5'-AGCTT CAC ACC CAC CAG GAC TTC CAG (SEQ ID NO: 36)
CCG GTG CTG CAC CTG

A GTG TGG GTG GTC CTG AAG GTC GGC    (SEQ ID NO: 38)
CAC GAC GTG-5'
DraIII
```

The first CAC in the duplex encodes the N-terminal histidine residue of the canine endostatin. The HindIII-XhoI fragment encoding the full-length canine endostatin thus could be ligated to the HindIII-XhoI digested pdCs-caFc vector (see Example 7) for expression. Stable NS/0 clones expressing caFc-caEndo were selected and assayed by anti-caFc ELISA, as described in Examples 2 and 3. The protein product was analyzed on SDS-PAGE and confirmed by Western blot analysis.

Example 9

Expression of caFc-caAngiostatin

The cDNA encoding the full length canine angiostatin (DNA sequence set forth in SEQ ID NO:39; amino acid sequence set forth in SEQ ID NO:40) was adapted for expression as a caFc fusion protein essentially as in the aforementioned examples. Briefly, at the 3' end, a STOP codon was introduced, for example, by PCR, immediately after the codon encoding the C-terminal lysine residue and this was followed by a NotI restriction site instead of an XhoI site, since there was an internal XhoI restriction site in the cDNA of the canine angiostatin. At the 5' end, a HindIII site was introduced in-frame immediately upstream of the N-terminus of angiostatin. The HindIII-NotI fragment encoding the full length canine angiostatin then was ligated to the HindIII-NotI digested pdCs-caFc vector (where the NotI site was introduced at the XhoI site through linker ligation) for expression. Stable NS/0 clones expressing caFc-caAngio were selected and assayed by anti-caFc ELISA, as described in Examples 2 and 3. The protein product was analyzed on SDS-PAGE and confirmed by Western blot analysis.

Example 10

Expression of muFc-K1 of muAngio

Angiostatin comprises the first four of the five Kringle domains of plasminogen. To determine if any one or several Kringle domains are responsible for the observed anti-angiogenic activity of angiostatin, it is possible to produce single Kringle domains by themselves or combination thereof for testing. To demonstrate the utility of Fc as a fusion protein partner, the expression of the first Kringle domain of murine angiostatin (K1) was achieved in the following way. The first Kringle domain ends at Glu-87 of murine angiostatin (SEQ ID NO:25). There was a convenient NsiI restriction site in the cDNA at this position so that after digestion by NsiI, the four-base 3'-overhang was removed by T4 polymerase to create a blunt end. A translation STOP codon was introduced immediately downstream of the GAA encoding Glu-87 via ligation to the palindromic linker TGA CTC GAG TCA (SEQ ID NO: 41), where the STOP codon TGA was followed by an XhoI site. The HindIII-XhoI fragment encoding this truncated angiostatin, i.e., first Kringle only, then was ligated into the pdCs-muFc($D_4K$) vector for expression. High levels of expression were obtained in both transient and stable expression, as analyzed by anti-muFc ELISA and SDS-PAGE.

Example 11

Expression of muFc-innerK1 of muAngio

A Kringle domain consists of multiple loops, including an outer loop and an inner loop. In the first Kringle of murine angiostatin, the inner loop is defined by Cys 55 and Cys 79, which together form a disulfide bond at the base of the loop. The Cys-67 of the inner loop forms another disulfide bond with a Cys residue of the outer loop to give the Kringle structure. To test if the inner loop has any anti-angiogenic activity, it was expressed as a muFc-inner K1 (Kringle 1) as follows. With a DNA fragment encoding the first Kringle as template, a mutagenic primer having the sequence 5'GGG CCT TGG AGC TAC ACT ACA (SEQ ID NO: 42; encoded amino acids disclosed in SEQ ID NO:43) was used to mutagenize TGC (Cys-67) to AGC (Ser), by PCR. This ensures that the Cys-67 does not form a disulfide bond when the inner loop of Kringle 1 is expressed without the outer loop. An upstream primer having the sequence 5'GCGGATCCAAGCTT AGT ACA CAT CCC AAT GAG GG (SEQ ID NO:44; encoded amino acids disclosed in SEQ ID NO:45) was used to introduce a HindIII site in frame immediately 5' to the codon for Ser-43 (AGT). A BamHI site was also introduced immediately upstream of the HindIII site. The BamHI site is useful for ligating to the BamHI site at the end of the flexible Gly-Ser linker shown in Example 12 below. Thus a HindIII-XhoI DNA fragment encoding Ser-43 through Glu-87 of murine angiostatin was ligated to the pdCs-muFc($D_4K$) vector for expression. High levels of expression of muFc-innerK1 were obtained in both transient and stable expression, as analyzed by anti-muFc ELISA and SDS-PAGE.

Example 12

Expression of muFc-muEndo-GlySer Linker-InnerK1 of muAngio

The hybrid molecule muFc-muEndo-innerK1 comprises muFc-muEndo joined by a polypeptide linker containing glycine and serine residues, to the inner loop of the first Kringle of murine angiostatin. The DNA construct was assembled as follows.

There is a BspHI site at the 3' end of the murine endostatin cDNA. To introduce a flexible linker of glycine and serine residues at the C-terminus of murine endostatin, a 540-bp HindIII-BspHI fragment encoding endostatin was ligated to an overlapping oligonucleotide duplex formed by the oligonucleotides disclosed in SEQ ID NO:46 and SEQ ID NO:48. The amino acid linker encoded by SEQ ID NO:46 is disclosed in SEQ ID NO:47.

The HindIII-BamHI fragment encoding murine endostatin and the Gly-Ser linker was subcloned into a standard cloning vector. The BamHI site was then used to introduce the BamHI-XhoI fragment encoding the innerK1 in Example 11. The resulting HindIII-XhoI fragment encoding muEndo-GlySer linker-innerK1, was ligated to the pdCs-muFc($D_4K$) vector for expression. High levels of expression of muFc-muEndo-GlySer linker-innerK1 were obtained in both transient and stable expression, as analyzed by anti-muFc ELISA and SDS-PAGE.

Example 13

Expression of muFc-muEndo-GlySer Linker-K1 of muAngio

The hybrid molecule muFc-muEndo-K1 comprises muFc-muEndo joined by a polypeptide linker containing glycine and serine residues, to the first Kringle of murine angiostatin. The DNA construct was assembled as follows.

The BamHI end of the HindIII-BamHI fragment encoding the muEndo-GlySer linker (Example 12) was ligated to the HindIII-XhoI fragment encoding the Kringle 1 of murine angiostatin (Example 10) via the following adaptor:

```
BamHI
5' GA TCC TCA GGC C          (SEQ ID NO: 49)
       G AGT CCG GTCGA       (SEQ ID NO: 50)
                  HindIII
```

The adaptor has a HindIII' sticky end, which upon ligation, would not regenerate the HindIII site. Thus, the resulting HindIII-XhoI fragment, which encodes the muEndo-GlySer linker-Kringle 1, was ligated to the pdCs-muFc($D_4K$) vector for expression. High levels of expression of muFc-muEndo-GlySer linker-K1 were obtained in both transient and stable expression, as analyzed by anti-muFc ELISA and SDS-PAGE.

Example 14

Expression of muFc-muEndo-GlySer Linker-muAngio

The hybrid molecule muFc-muEndo-GlySer linker-muAngio comprises muFc-muEndo joined by a polypeptide linker containing glycine and serine residues, to murine angiostatin. The DNA construct was assembled essentially as follows. The BamHI end of the HindIII-BamHI fragment encoding the muEndo-GlySer linker (Example 12) was ligated to the HindIII-XhoI fragment encoding murine angiostatin via the adaptor described in Example 13. The resulting HindIII-XhoI fragment, which encodes the muEndo-GlySer linker-muAngio, was ligated to the pdCs-muFc($D_4$K) vector for expression. High levels of expression of muFc-muEndo-GlySer linker-muAngio were obtained in both transient and stable expression, as analyzed by anti-muFc ELISA and SDS-PAGE.

Example 15

Expression of huAngio-huFc-huEndo

The hybrid molecule huAngio-huFc-huEndo comprises human angiostatin joined by a peptide bond to huFc-huEndo. The DNA construct was assembled as follows. A HindIII-XhoI fragment which encodes human angiostatin without a STOP codon was first generated by PCR, so that the codon for the last amino acid residue of angiostatin was followed immediately by CTCGAG of the XhoI site. The HindIII at the 5' end was ligated to an XbaI-AflII fragment of the light chain signal peptide (Lo et al., Protein Engineering (1998) 11:495) via a AflII-HindIII' adaptor:

```
AfIII
5' TTA AGC GGC C              (SEQ ID NO: 51)
       CG CGG GTCGA           (SEQ ID NO: 52)
              HindIII'
```

The HindIII' sticky end of the adaptor, upon ligation, would not regenerate a HindIII site. At the 3' end, the XhoI site was ligated to the AflII site of the AflII-XhoI fragment encoding the huFc-hu-Endo via the following XhoI'-AflII adaptor:

```
XhoI'
5' TC GAC TCC GGC             (SEQ ID NO: 53)
        G AGG CCG AATT        (SEQ ID NO: 54)
                AfIII
```

The XhoI sticky end of the adaptor, upon ligation, would not regenerate a XhoI site. The resulting XbaI-XhoI fragment encoding the signal peptide-human angiostatin-huFc-human endostatin was cloned into the pdCs vector for expression. High levels of expression of were obtained in both transient and stable expression, as analyzed by anti-muFc ELISA and SDS-PAGE.

Example 16

Pharmacokinetics

In one set of pharmacokinetic studies, C57/BL6 mice with implanted Lewis lung tumors at 100-200 $mm^3$ were injected in the tail vein with 720 μg huFc-huAngio per mouse. The size of the tumors and the dosage of huFc-huAngio used in this study were chosen to simulate the actual treatment protocol described by O'Reilly (O'Reilly et al., (1996) Nature Medicine 2:689). Blood was harvested by retro-orbital bleeding at ½, 1, 2, 4, 8, 24, and 48 hr. post injection. The blood samples were analyzed by anti-huFc ELISA followed by Western analysis. HuFc-huAngio was found to have a circulating half-life of about 32 hr. in mouse and Western analysis showed that over 90% of the hu-Fc-huAngio remained as an intact molecule in circulation.

The pharmacokinetic studies was also repeated in Swiss mice without tumors at a dosage of 200 μg/mouse. In this case huFc-huAngio was found to have a circulating half-life of about 33 hr.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A homodimeric protein having angiogenesis inhibiting activity, which consists of two identical fusion proteins bound together as a homodimer, each fusion protein comprising an immunoglobulin Fc region and an endostatin protein linked to the immunoglobulin Fc region; the immunoglobulin Fc region comprising a hinge region, a CH2 region, and a CH3 region, wherein the endostatin has the amino acid sequence of SEQ ID NO: 4.

2. The homodimeric protein of claim 1 wherein the immunoglobulin Fc region is an IgG1 Fc region.

3. The homodimeric protein of claim 1 wherein the endostatin protein is linked to the C-terminal end of the immunoglobulin Fc region.

4. The homodimeric protein of claim 1 wherein the endostatin protein is linked to the N-terminal end of the immunoglobulin Fc region.

* * * * *

SEQUENCE LISTING

```
<160> NUMBER OF SEQ ID NOS: 54

<210> SEQ ID NO 1
<211> LENGTH: 696
<212> TYPE: DNA
<213> ORGANISM: Homo sapiens
<220> FEATURE:
<221> NAME/KEY: CDS
<222> LOCATION: (1)..(696)
<223> OTHER INFORMATION: Fc fragment of the human immunoglobulin gamma

<400> SEQUENCE: 1

gag ccc aaa tct tct gac aaa act cac aca tgc cca ccg tgc cca gca       48
Glu Pro Lys Ser Ser Asp Lys Thr His Thr Cys Pro Pro Cys Pro Ala
  1               5                  10                  15

cct gaa ctc ctg ggg gga ccg tca gtc ttc ctc ttc ccc cca aaa ccc       96
Pro Glu Leu Leu Gly Gly Pro Ser Val Phe Leu Phe Pro Pro Lys Pro
             20                  25                  30
```

```
aag gac acc ctc atg atc tcc cgg acc cct gag gtc aca tgc gtg gtg      144
Lys Asp Thr Leu Met Ile Ser Arg Thr Pro Glu Val Thr Cys Val Val
        35                  40                  45

gtg gac gtg agc cac gaa gac cct gag gtc aag ttc aac tgg tac gtg      192
Val Asp Val Ser His Glu Asp Pro Glu Val Lys Phe Asn Trp Tyr Val
    50                  55                  60

gac ggc gtg gag gtg cat aat gcc aag aca aag ccg cgg gag gag cag      240
Asp Gly Val Glu Val His Asn Ala Lys Thr Lys Pro Arg Glu Glu Gln
65                  70                  75                  80

tac aac agc acg tac cgt gtg gtc agc gtc ctc acc gtc ctg cac cag      288
Tyr Asn Ser Thr Tyr Arg Val Val Ser Val Leu Thr Val Leu His Gln
                85                  90                  95

gac tgg ctg aat ggc aag gag tac aag tgc aag gtc tcc aac aaa gcc      336
Asp Trp Leu Asn Gly Lys Glu Tyr Lys Cys Lys Val Ser Asn Lys Ala
            100                 105                 110

ctc cca gcc ccc atc gag aaa acc atc tcc aaa gcc aaa ggg cag ccc      384
Leu Pro Ala Pro Ile Glu Lys Thr Ile Ser Lys Ala Lys Gly Gln Pro
        115                 120                 125

cga gaa cca cag gtg tac acc ctg ccc cca tca cgg gag gag atg acc      432
Arg Glu Pro Gln Val Tyr Thr Leu Pro Pro Ser Arg Glu Glu Met Thr
    130                 135                 140

aag aac cag gtc agc ctg acc tgc ctg gtc aaa ggc ttc tat ccc agc      480
Lys Asn Gln Val Ser Leu Thr Cys Leu Val Lys Gly Phe Tyr Pro Ser
145                 150                 155                 160

gac atc gcc gtg gag tgg gag agc aat ggg cag ccg gag aac aac tac      528
Asp Ile Ala Val Glu Trp Glu Ser Asn Gly Gln Pro Glu Asn Asn Tyr
                165                 170                 175

aag acc acg cct ccc gtg ctg gac tcc gac ggc tcc ttc ttc ctc tat      576
Lys Thr Thr Pro Pro Val Leu Asp Ser Asp Gly Ser Phe Phe Leu Tyr
            180                 185                 190

agc aag ctc acc gtg gac aag agc agg tgg cag cag ggg aac gtc ttc      624
Ser Lys Leu Thr Val Asp Lys Ser Arg Trp Gln Gln Gly Asn Val Phe
        195                 200                 205

tca tgc tcc gtg atg cat gag gct ctg cac aac cac tac acg cag aag      672
Ser Cys Ser Val Met His Glu Ala Leu His Asn His Tyr Thr Gln Lys
    210                 215                 220

agc ctc tcc ctg tcc ccg ggt aaa                                      696
Ser Leu Ser Leu Ser Pro Gly Lys
225                 230


<210> SEQ ID NO 2
<211> LENGTH: 232
<212> TYPE: PRT
<213> ORGANISM: Homo sapiens

<400> SEQUENCE: 2

Glu Pro Lys Ser Ser Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
```

```
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 3
<211> LENGTH: 549
<212> TYPE: DNA
<213> ORGANISM: Homo sapiens
<220> FEATURE:
<221> NAME/KEY: CDS
<222> LOCATION: (1)..(549)
<223> OTHER INFORMATION: endostatin

<400> SEQUENCE: 3

cac agc cac cgc gac ttc cag ccg gtg ctc cac ctg gtt gcg ctc aac       48
His Ser His Arg Asp Phe Gln Pro Val Leu His Leu Val Ala Leu Asn
  1               5                  10                  15

agc ccc ctg tca ggc ggc atg cgg ggc atc cgc ggg gcc gac ttc cag       96
Ser Pro Leu Ser Gly Gly Met Arg Gly Ile Arg Gly Ala Asp Phe Gln
            20                  25                  30

tgc ttc cag cag gcg cgg gcc gtg ggg ctg gcg ggc acc ttc cgc gcc      144
Cys Phe Gln Gln Ala Arg Ala Val Gly Leu Ala Gly Thr Phe Arg Ala
        35                  40                  45

ttc ctg tcc tcg cgc ctg cag gac ctg tac agc atc gtg cgc cgt gcc      192
Phe Leu Ser Ser Arg Leu Gln Asp Leu Tyr Ser Ile Val Arg Arg Ala
     50                  55                  60

gac cgc gca gcc gtg ccc atc gtc aac ctc aag gac gag ctg ctg ttt      240
Asp Arg Ala Ala Val Pro Ile Val Asn Leu Lys Asp Glu Leu Leu Phe
 65                  70                  75                  80

ccc agc tgg gag gct ctg ttc tca ggc tct gag ggt ccg ctg aag ccc      288
Pro Ser Trp Glu Ala Leu Phe Ser Gly Ser Glu Gly Pro Leu Lys Pro
                85                  90                  95

ggg gca cgc atc ttc tcc ttt gac ggc aag gac gtc ctg agg cac ccc      336
Gly Ala Arg Ile Phe Ser Phe Asp Gly Lys Asp Val Leu Arg His Pro
            100                 105                 110

acc tgg ccc cag aag agc gtg tgg cat ggc tcg gac ccc aac ggg cgc      384
Thr Trp Pro Gln Lys Ser Val Trp His Gly Ser Asp Pro Asn Gly Arg
        115                 120                 125

agg ctg acc gag agc tac tgt gag acg tgg cgg acg gag gct ccc tcg      432
Arg Leu Thr Glu Ser Tyr Cys Glu Thr Trp Arg Thr Glu Ala Pro Ser
    130                 135                 140

gcc acg ggc cag gcc tcc tcg ctg ctg ggg ggc agg ctc ctg ggg cag      480
Ala Thr Gly Gln Ala Ser Ser Leu Leu Gly Gly Arg Leu Leu Gly Gln
145                 150                 155                 160

agt gcc gcg agc tgc cat cac gcc tac atc gtg ctc tgc att gag aac      528
Ser Ala Ala Ser Cys His His Ala Tyr Ile Val Leu Cys Ile Glu Asn
```

```
                165                 170                 175

agc ttc atg act gcc tcc aag                                          549
Ser Phe Met Thr Ala Ser Lys
            180


<210> SEQ ID NO 4
<211> LENGTH: 183
<212> TYPE: PRT
<213> ORGANISM: Homo sapiens

<400> SEQUENCE: 4

His Ser His Arg Asp Phe Gln Pro Val Leu His Leu Val Ala Leu Asn
  1               5                  10                  15

Ser Pro Leu Ser Gly Gly Met Arg Gly Ile Arg Gly Ala Asp Phe Gln
            20                  25                  30

Cys Phe Gln Gln Ala Arg Ala Val Gly Leu Ala Gly Thr Phe Arg Ala
        35                  40                  45

Phe Leu Ser Ser Arg Leu Gln Asp Leu Tyr Ser Ile Val Arg Arg Ala
    50                  55                  60

Asp Arg Ala Ala Val Pro Ile Val Asn Leu Lys Asp Glu Leu Leu Phe
 65                  70                  75                  80

Pro Ser Trp Glu Ala Leu Phe Ser Gly Ser Glu Gly Pro Leu Lys Pro
                85                  90                  95

Gly Ala Arg Ile Phe Ser Phe Asp Gly Lys Asp Val Leu Arg His Pro
            100                 105                 110

Thr Trp Pro Gln Lys Ser Val Trp His Gly Ser Asp Pro Asn Gly Arg
        115                 120                 125

Arg Leu Thr Glu Ser Tyr Cys Glu Thr Trp Arg Thr Glu Ala Pro Ser
    130                 135                 140

Ala Thr Gly Gln Ala Ser Ser Leu Leu Gly Gly Arg Leu Leu Gly Gln
145                 150                 155                 160

Ser Ala Ala Ser Cys His His Ala Tyr Ile Val Leu Cys Ile Glu Asn
                165                 170                 175

Ser Phe Met Thr Ala Ser Lys
            180


<210> SEQ ID NO 5
<211> LENGTH: 30
<212> TYPE: DNA
<213> ORGANISM: Artificial Sequence
<220> FEATURE:
<223> OTHER INFORMATION: Description of Artificial Sequence:Forward
      primer for human Fc-Endo
<220> FEATURE:
<221> NAME/KEY: CDS
<222> LOCATION: (3)..(29)

<400> SEQUENCE: 5

cc ccg ggt aaa cac agc cac cgc gac ttc c                             30
   Pro Gly Lys His Ser His Arg Asp Phe
     1               5


<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: human
      Fc-Endo peptide

<400> SEQUENCE: 6

Pro Gly Lys His Ser His Arg Asp Phe
```

```
  1               5


<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence:Forward
      primer for human Fc-endo
<220> FEATURE:
<221> NAME/KEY: CDS
<222> LOCATION: (2)..(25)

<400> SEQUENCE: 7

c aag ctt cac agc cac cgc gac ttc c                                    26
  Lys Leu His Ser His Arg Asp Phe
    1               5


<210> SEQ ID NO 8
<211> LENGTH: 8
<212> TYPE: PRT
<213> ORGANISM: Artificial Sequence
<220> FEATURE:
<223> OTHER INFORMATION: Description of Artificial Sequence: human
      Fc-Endo peptide

<400> SEQUENCE: 8

Lys Leu His Ser His Arg Asp Phe
  1               5


<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence:Reverse
      primer for human Fc-Endo

<400> SEQUENCE: 9

cctcgagcta cttggaggca gtcatg                                           26


<210> SEQ ID NO 10
<211> LENGTH: 1089
<212> TYPE: DNA
<213> ORGANISM: Homo sapiens
<220> FEATURE:
<221> NAME/KEY: CDS
<222> LOCATION: (1)..(1089)
<223> OTHER INFORMATION: angiostatin

<400> SEQUENCE: 10

aaa gtg tat ctc tca gag tgc aag act ggg aat gga aag aac tac aga       48
Lys Val Tyr Leu Ser Glu Cys Lys Thr Gly Asn Gly Lys Asn Tyr Arg
  1               5                  10                  15

ggg acg atg tcc aaa aca aaa aat ggc atc acc tgt caa aaa tgg agt       96
Gly Thr Met Ser Lys Thr Lys Asn Gly Ile Thr Cys Gln Lys Trp Ser
             20                  25                  30

tcc act tct ccc cac aga cct aga ttc tca cct gct aca cac ccc tca      144
Ser Thr Ser Pro His Arg Pro Arg Phe Ser Pro Ala Thr His Pro Ser
         35                  40                  45

gag gga ctg gag gag aac tac tgc agg aat cca gac aac gat ccg cag      192
Glu Gly Leu Glu Glu Asn Tyr Cys Arg Asn Pro Asp Asn Asp Pro Gln
     50                  55                  60

ggg ccc tgg tgc tat act act gat cca gaa aag aga tat gac tac tgc      240
Gly Pro Trp Cys Tyr Thr Thr Asp Pro Glu Lys Arg Tyr Asp Tyr Cys
 65                  70                  75                  80

gac att ctt gag tgt gaa gag gaa tgt atg cat tgc agt gga gaa aac      288
```

```
Asp Ile Leu Glu Cys Glu Glu Glu Cys Met His Cys Ser Gly Glu Asn
                 85                  90                  95

tat gac ggc aaa att tcc aag acc atg tct gga ctg gaa tgc cag gcc      336
Tyr Asp Gly Lys Ile Ser Lys Thr Met Ser Gly Leu Glu Cys Gln Ala
            100                 105                 110

tgg gac tct cag agc cca cac gct cat gga tac att cct tcc aaa ttt      384
Trp Asp Ser Gln Ser Pro His Ala His Gly Tyr Ile Pro Ser Lys Phe
        115                 120                 125

cca aac aag aac ctg aag aag aat tac tgt cgt aac ccc gat agg gag      432
Pro Asn Lys Asn Leu Lys Lys Asn Tyr Cys Arg Asn Pro Asp Arg Glu
    130                 135                 140

ctg cgg cct tgg tgt ttc acc acc gac ccc aac aag cgc tgg gaa ctt      480
Leu Arg Pro Trp Cys Phe Thr Thr Asp Pro Asn Lys Arg Trp Glu Leu
145                 150                 155                 160

tgc gac atc ccc cgc tgc aca aca cct cca cca tct tct ggt ccc acc      528
Cys Asp Ile Pro Arg Cys Thr Thr Pro Pro Pro Ser Ser Gly Pro Thr
                165                 170                 175

tac cag tgt ctg aag gga aca ggt gaa aac tat cgc ggg aat gtg gct      576
Tyr Gln Cys Leu Lys Gly Thr Gly Glu Asn Tyr Arg Gly Asn Val Ala
            180                 185                 190

gtt acc gtt tcc ggg cac acc tgt cag cac tgg agt gca cag acc cct      624
Val Thr Val Ser Gly His Thr Cys Gln His Trp Ser Ala Gln Thr Pro
        195                 200                 205

cac aca cat aac agg aca cca gaa aac ttc ccc tgc aaa aat ttg gat      672
His Thr His Asn Arg Thr Pro Glu Asn Phe Pro Cys Lys Asn Leu Asp
    210                 215                 220

gaa aac tac tgc cgc aat cct gac gga aaa agg gcc cca tgg tgc cat      720
Glu Asn Tyr Cys Arg Asn Pro Asp Gly Lys Arg Ala Pro Trp Cys His
225                 230                 235                 240

aca acc aac agc caa gtg cgg tgg gag tac tgt aag ata ccg tcc tgt      768
Thr Thr Asn Ser Gln Val Arg Trp Glu Tyr Cys Lys Ile Pro Ser Cys
                245                 250                 255

gac tcc tcc cca gta tcc acg gaa caa ttg gct ccc aca gca cca cct      816
Asp Ser Ser Pro Val Ser Thr Glu Gln Leu Ala Pro Thr Ala Pro Pro
            260                 265                 270

gag cta acc cct gtg gtc cag gac tgc tac cat ggt gat gga cag agc      864
Glu Leu Thr Pro Val Val Gln Asp Cys Tyr His Gly Asp Gly Gln Ser
        275                 280                 285

tac cga ggc aca tcc tcc acc acc acc aca gga aag aag tgt cag tct      912
Tyr Arg Gly Thr Ser Ser Thr Thr Thr Thr Gly Lys Lys Cys Gln Ser
    290                 295                 300

tgg tca tct atg aca cca cac cgg cac cag aag acc cca gaa aac tac      960
Trp Ser Ser Met Thr Pro His Arg His Gln Lys Thr Pro Glu Asn Tyr
305                 310                 315                 320

cca aat gct ggc ctg aca atg aac tac tgc agg aat cca gat gcc gat     1008
Pro Asn Ala Gly Leu Thr Met Asn Tyr Cys Arg Asn Pro Asp Ala Asp
                325                 330                 335

aaa ggc ccc tgg tgt ttt acc aca gac ccc agc gtc agg tgg gag tac     1056
Lys Gly Pro Trp Cys Phe Thr Thr Asp Pro Ser Val Arg Trp Glu Tyr
            340                 345                 350

tgc aac ctg aaa aaa tgc tca gga aca gaa gcg                         1089
Cys Asn Leu Lys Lys Cys Ser Gly Thr Glu Ala
        355                 360


<210> SEQ ID NO 11
<211> LENGTH: 363
<212> TYPE: PRT
<213> ORGANISM: Homo sapiens

<400> SEQUENCE: 11

Lys Val Tyr Leu Ser Glu Cys Lys Thr Gly Asn Gly Lys Asn Tyr Arg
```

```
1               5                   10                  15

Gly Thr Met Ser Lys Thr Lys Asn Gly Ile Thr Cys Gln Lys Trp Ser
            20                  25                  30

Ser Thr Ser Pro His Arg Pro Arg Phe Ser Pro Ala Thr His Pro Ser
        35                  40                  45

Glu Gly Leu Glu Glu Asn Tyr Cys Arg Asn Pro Asp Asn Asp Pro Gln
    50                  55                  60

Gly Pro Trp Cys Tyr Thr Thr Asp Pro Glu Lys Arg Tyr Asp Tyr Cys
65                  70                  75                  80

Asp Ile Leu Glu Cys Glu Glu Glu Cys Met His Cys Ser Gly Glu Asn
                85                  90                  95

Tyr Asp Gly Lys Ile Ser Lys Thr Met Ser Gly Leu Glu Cys Gln Ala
            100                 105                 110

Trp Asp Ser Gln Ser Pro His Ala His Gly Tyr Ile Pro Ser Lys Phe
        115                 120                 125

Pro Asn Lys Asn Leu Lys Lys Asn Tyr Cys Arg Asn Pro Asp Arg Glu
    130                 135                 140

Leu Arg Pro Trp Cys Phe Thr Thr Asp Pro Asn Lys Arg Trp Glu Leu
145                 150                 155                 160

Cys Asp Ile Pro Arg Cys Thr Thr Pro Pro Pro Ser Ser Gly Pro Thr
                165                 170                 175

Tyr Gln Cys Leu Lys Gly Thr Gly Glu Asn Tyr Arg Gly Asn Val Ala
            180                 185                 190

Val Thr Val Ser Gly His Thr Cys Gln His Trp Ser Ala Gln Thr Pro
        195                 200                 205

His Thr His Asn Arg Thr Pro Glu Asn Phe Pro Cys Lys Asn Leu Asp
    210                 215                 220

Glu Asn Tyr Cys Arg Asn Pro Asp Gly Lys Arg Ala Pro Trp Cys His
225                 230                 235                 240

Thr Thr Asn Ser Gln Val Arg Trp Glu Tyr Cys Lys Ile Pro Ser Cys
                245                 250                 255

Asp Ser Ser Pro Val Ser Thr Glu Gln Leu Ala Pro Thr Ala Pro Pro
            260                 265                 270

Glu Leu Thr Pro Val Val Gln Asp Cys Tyr His Gly Asp Gly Gln Ser
        275                 280                 285

Tyr Arg Gly Thr Ser Ser Thr Thr Thr Thr Gly Lys Lys Cys Gln Ser
    290                 295                 300

Trp Ser Ser Met Thr Pro His Arg His Gln Lys Thr Pro Glu Asn Tyr
305                 310                 315                 320

Pro Asn Ala Gly Leu Thr Met Asn Tyr Cys Arg Asn Pro Asp Ala Asp
                325                 330                 335

Lys Gly Pro Trp Cys Phe Thr Thr Asp Pro Ser Val Arg Trp Glu Tyr
            340                 345                 350

Cys Asn Leu Lys Lys Cys Ser Gly Thr Glu Ala
        355                 360
```

```
<210> SEQ ID NO 12
<211> LENGTH: 29
<212> TYPE: DNA
<213> ORGANISM: Artificial Sequence
<220> FEATURE:
<223> OTHER INFORMATION: Description of Artificial Sequence:Forward
      primer for human Fc-Angio
<220> FEATURE:
<221> NAME/KEY: CDS
<222> LOCATION: (3)..(29)
```

<400> SEQUENCE: 12

```
cc ccg ggt aag aaa gtg tat ctc tca gag                         29
   Pro Gly Lys Lys Val Tyr Leu Ser Glu
     1               5
```

<210> SEQ ID NO 13
<211> LENGTH: 9
<212> TYPE: PRT
<213> ORGANISM: Artificial Sequence
<220> FEATURE:
<223> OTHER INFORMATION: Description of Artificial Sequence: human Fc-Angio peptide

<400> SEQUENCE: 13

```
Pro Gly Lys Lys Val Tyr Leu Ser Glu
  1               5
```

<210> SEQ ID NO 14
<211> LENGTH: 28
<212> TYPE: DNA
<213> ORGANISM: Artificial Sequence
<220> FEATURE:
<223> OTHER INFORMATION: Description of Artificial Sequence:Forward primer for human Fc-Angio
<220> FEATURE:
<221> NAME/KEY: CDS
<222> LOCATION: (2)..(28)

<400> SEQUENCE: 14

```
c ccc aag ctt aaa gtg tat ctc tca gag                          28
  Pro Lys Leu Lys Val Tyr Leu Ser Glu
    1               5
```

<210> SEQ ID NO 15
<211> LENGTH: 9
<212> TYPE: PRT
<213> ORGANISM: Artificial Sequence
<220> FEATURE:
<223> OTHER INFORMATION: Description of Artificial Sequence: human Fc-Angio peptide

<400> SEQUENCE: 15

```
Pro Lys Leu Lys Val Tyr Leu Ser Glu
  1               5
```

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence:Reverse primer for human Fc-Angio

<400> SEQUENCE: 16

```
cccctcgagc tacgcttctg ttcctgagca                               30
```

<210> SEQ ID NO 17
<211> LENGTH: 552
<212> TYPE: DNA
<213> ORGANISM: Mus musculus
<220> FEATURE:
<221> NAME/KEY: CDS
<222> LOCATION: (1)..(552)
<223> OTHER INFORMATION: endostatin

<400> SEQUENCE: 17

```
cat act cat cag gac ttt cag cca gtg ctc cac ctg gtg gca ctg aac      48
His Thr His Gln Asp Phe Gln Pro Val Leu His Leu Val Ala Leu Asn
  1               5                  10                  15
```

```
acc ccc ctg tct gga ggc atg cgt ggt atc cgt gga gca gat ttc cag        96
Thr Pro Leu Ser Gly Gly Met Arg Gly Ile Arg Gly Ala Asp Phe Gln
            20                  25                  30

tgc ttc cag caa gcc cga gcc gtg ggg ctg tcg ggc acc ttc cgg gct       144
Cys Phe Gln Gln Ala Arg Ala Val Gly Leu Ser Gly Thr Phe Arg Ala
        35                  40                  45

ttc ctg tcc tct agg ctg cag gat ctc tat agc atc gtg cgc cgt gct       192
Phe Leu Ser Ser Arg Leu Gln Asp Leu Tyr Ser Ile Val Arg Arg Ala
    50                  55                  60

gac cgg ggg tct gtg ccc atc gtc aac ctg aag gac gag gtg cta tct       240
Asp Arg Gly Ser Val Pro Ile Val Asn Leu Lys Asp Glu Val Leu Ser
 65                  70                  75                  80

ccc agc tgg gac tcc ctg ttt tct ggc tcc cag ggt caa gtg caa ccc       288
Pro Ser Trp Asp Ser Leu Phe Ser Gly Ser Gln Gly Gln Val Gln Pro
                85                  90                  95

ggg gcc cgc atc ttt tct ttt gac ggc aga gat gtc ctg aga cac cca       336
Gly Ala Arg Ile Phe Ser Phe Asp Gly Arg Asp Val Leu Arg His Pro
            100                 105                 110

gcc tgg ccg cag aag agc gta tgg cac ggc tcg gac ccc agt ggg cgg       384
Ala Trp Pro Gln Lys Ser Val Trp His Gly Ser Asp Pro Ser Gly Arg
        115                 120                 125

agg ctg atg gag agt tac tgt gag aca tgg cga act gaa act act ggg       432
Arg Leu Met Glu Ser Tyr Cys Glu Thr Trp Arg Thr Glu Thr Thr Gly
    130                 135                 140

gct aca ggt cag gcc tcc tcc ctg ctg tca ggc agg ctc ctg gaa cag       480
Ala Thr Gly Gln Ala Ser Ser Leu Leu Ser Gly Arg Leu Leu Glu Gln
145                 150                 155                 160

aaa gct gcg agc tgc cac aac agc tac atc gtc ctg tgc att gag aat       528
Lys Ala Ala Ser Cys His Asn Ser Tyr Ile Val Leu Cys Ile Glu Asn
                165                 170                 175

agc ttc atg acc tct ttc tcc aaa                                       552
Ser Phe Met Thr Ser Phe Ser Lys
            180


<210> SEQ ID NO 18
<211> LENGTH: 184
<212> TYPE: PRT
<213> ORGANISM: Mus musculus

<400> SEQUENCE: 18

His Thr His Gln Asp Phe Gln Pro Val Leu His Leu Val Ala Leu Asn
  1               5                  10                  15

Thr Pro Leu Ser Gly Gly Met Arg Gly Ile Arg Gly Ala Asp Phe Gln
            20                  25                  30

Cys Phe Gln Gln Ala Arg Ala Val Gly Leu Ser Gly Thr Phe Arg Ala
        35                  40                  45

Phe Leu Ser Ser Arg Leu Gln Asp Leu Tyr Ser Ile Val Arg Arg Ala
    50                  55                  60

Asp Arg Gly Ser Val Pro Ile Val Asn Leu Lys Asp Glu Val Leu Ser
 65                  70                  75                  80

Pro Ser Trp Asp Ser Leu Phe Ser Gly Ser Gln Gly Gln Val Gln Pro
                85                  90                  95

Gly Ala Arg Ile Phe Ser Phe Asp Gly Arg Asp Val Leu Arg His Pro
            100                 105                 110

Ala Trp Pro Gln Lys Ser Val Trp His Gly Ser Asp Pro Ser Gly Arg
        115                 120                 125

Arg Leu Met Glu Ser Tyr Cys Glu Thr Trp Arg Thr Glu Thr Thr Gly
    130                 135                 140
```

```
Ala Thr Gly Gln Ala Ser Ser Leu Leu Ser Gly Arg Leu Leu Glu Gln
145                 150                 155                 160

Lys Ala Ala Ser Cys His Asn Ser Tyr Ile Val Leu Cys Ile Glu Asn
                165                 170                 175

Ser Phe Met Thr Ser Phe Ser Lys
            180


<210> SEQ ID NO 19
<211> LENGTH: 699
<212> TYPE: DNA
<213> ORGANISM: Mus musculus
<220> FEATURE:
<221> NAME/KEY: CDS
<222> LOCATION: (1)..(699)
<223> OTHER INFORMATION: Fc

<400> SEQUENCE: 19

gag ccc aga ggg ccc aca atc aag ccc tgt cct cca tgc aaa tgc cca       48
Glu Pro Arg Gly Pro Thr Ile Lys Pro Cys Pro Pro Cys Lys Cys Pro
  1               5                  10                  15

gca cct aac ctc ttg ggt gga cca tcc gtc ttc atc ttc cct cca aag       96
Ala Pro Asn Leu Leu Gly Gly Pro Ser Val Phe Ile Phe Pro Pro Lys
             20                  25                  30

atc aag gat gta ctc atg atc tcc ctg agc ccc ata gtc aca tgt gtg      144
Ile Lys Asp Val Leu Met Ile Ser Leu Ser Pro Ile Val Thr Cys Val
         35                  40                  45

gtg gtg gat gtg agc gag gat gac cca gat gtc cag atc agc tgg ttt      192
Val Val Asp Val Ser Glu Asp Asp Pro Asp Val Gln Ile Ser Trp Phe
     50                  55                  60

gtg aac aac gtg gaa gta cac aca gct cag aca caa acc cat aga gag      240
Val Asn Asn Val Glu Val His Thr Ala Gln Thr Gln Thr His Arg Glu
 65                  70                  75                  80

gat tac aac agt act ctc cgg gtg gtc agt gcc ctc ccc atc cag cac      288
Asp Tyr Asn Ser Thr Leu Arg Val Val Ser Ala Leu Pro Ile Gln His
                 85                  90                  95

cag gac tgg atg agt ggc aag gag ttc aaa tgc aag gtc aac aac aaa      336
Gln Asp Trp Met Ser Gly Lys Glu Phe Lys Cys Lys Val Asn Asn Lys
            100                 105                 110

gac ctc cca gcg ccc atc gag aga acc atc tca aaa ccc aaa ggg tca      384
Asp Leu Pro Ala Pro Ile Glu Arg Thr Ile Ser Lys Pro Lys Gly Ser
        115                 120                 125

gta aga gct cca cag gta tat gtc ttg cct cca cca gaa gaa gag atg      432
Val Arg Ala Pro Gln Val Tyr Val Leu Pro Pro Pro Glu Glu Glu Met
    130                 135                 140

act aag aaa cag gtc act ctg acc tgc atg gtc aca gac ttc atg cct      480
Thr Lys Lys Gln Val Thr Leu Thr Cys Met Val Thr Asp Phe Met Pro
145                 150                 155                 160

gaa gac att tac gtg gag tgg acc aac aac ggg aaa aca gag cta aac      528
Glu Asp Ile Tyr Val Glu Trp Thr Asn Asn Gly Lys Thr Glu Leu Asn
                165                 170                 175

tac aag aac act gaa cca gtc ctg gac tct gat ggt tct tac ttc atg      576
Tyr Lys Asn Thr Glu Pro Val Leu Asp Ser Asp Gly Ser Tyr Phe Met
            180                 185                 190

tac agc aag ctg aga gtg gaa aag aag aac tgg gtg gaa aga aat agc      624
Tyr Ser Lys Leu Arg Val Glu Lys Lys Asn Trp Val Glu Arg Asn Ser
        195                 200                 205

tac tcc tgt tca gtg gtc cac gag ggt ctg cac aat cac cac acg act      672
Tyr Ser Cys Ser Val Val His Glu Gly Leu His Asn His His Thr Thr
    210                 215                 220

aag agc ttc tcc cgg acc ccg ggt aaa                                  699
Lys Ser Phe Ser Arg Thr Pro Gly Lys
225                 230
```

```
<210> SEQ ID NO 20
<211> LENGTH: 233
<212> TYPE: PRT
<213> ORGANISM: Mus musculus

<400> SEQUENCE: 20

Glu Pro Arg Gly Pro Thr Ile Lys Pro Cys Pro Pro Cys Lys Cys Pro
  1               5                  10                  15

Ala Pro Asn Leu Leu Gly Gly Pro Ser Val Phe Ile Phe Pro Pro Lys
             20                  25                  30

Ile Lys Asp Val Leu Met Ile Ser Leu Ser Pro Ile Val Thr Cys Val
         35                  40                  45

Val Val Asp Val Ser Glu Asp Asp Pro Asp Val Gln Ile Ser Trp Phe
     50                  55                  60

Val Asn Asn Val Glu Val His Thr Ala Gln Thr Gln Thr His Arg Glu
 65                  70                  75                  80

Asp Tyr Asn Ser Thr Leu Arg Val Val Ser Ala Leu Pro Ile Gln His
                 85                  90                  95

Gln Asp Trp Met Ser Gly Lys Glu Phe Lys Cys Lys Val Asn Asn Lys
            100                 105                 110

Asp Leu Pro Ala Pro Ile Glu Arg Thr Ile Ser Lys Pro Lys Gly Ser
        115                 120                 125

Val Arg Ala Pro Gln Val Tyr Val Leu Pro Pro Pro Glu Glu Glu Met
    130                 135                 140

Thr Lys Lys Gln Val Thr Leu Thr Cys Met Val Thr Asp Phe Met Pro
145                 150                 155                 160

Glu Asp Ile Tyr Val Glu Trp Thr Asn Asn Gly Lys Thr Glu Leu Asn
                165                 170                 175

Tyr Lys Asn Thr Glu Pro Val Leu Asp Ser Asp Gly Ser Tyr Phe Met
            180                 185                 190

Tyr Ser Lys Leu Arg Val Glu Lys Lys Asn Trp Val Glu Arg Asn Ser
        195                 200                 205

Tyr Ser Cys Ser Val Val His Glu Gly Leu His Asn His His Thr Thr
    210                 215                 220

Lys Ser Phe Ser Arg Thr Pro Gly Lys
225                 230


<210> SEQ ID NO 21
<211> LENGTH: 29
<212> TYPE: DNA
<213> ORGANISM: Artificial Sequence
<220> FEATURE:
<223> OTHER INFORMATION: Description of Artificial Sequence:Forward
      primer for mouse Fc-Endo
<220> FEATURE:
<221> NAME/KEY: CDS
<222> LOCATION: (2)..(28)

<400> SEQUENCE: 21

c ccc aag ctt cat act cat cag gac ttt c                                29
  Pro Lys Leu His Thr His Gln Asp Phe
    1               5


<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: mouse
      Fc-Endo peptide
```

<400> SEQUENCE: 22

```
Pro Lys Leu His Thr His Gln Asp Phe
  1               5
```

<210> SEQ ID NO 23
<211> LENGTH: 28
<212> TYPE: DNA
<213> ORGANISM: Artificial Sequence
<220> FEATURE:
<223> OTHER INFORMATION: Description of Artificial Sequence:Reverse primer for mouse Fc-Endo

<400> SEQUENCE: 23

```
cccctcgagc tatttggaga aagaggtc                                          28
```

<210> SEQ ID NO 24
<211> LENGTH: 1086
<212> TYPE: DNA
<213> ORGANISM: Mus musculus
<220> FEATURE:
<221> NAME/KEY: CDS
<222> LOCATION: (1)..(1086)
<223> OTHER INFORMATION: Angiostatin

<400> SEQUENCE: 24

```
gtg tat ctg tca gaa tgt aag acc ggc atc ggc aac ggc tac aga gga       48
Val Tyr Leu Ser Glu Cys Lys Thr Gly Ile Gly Asn Gly Tyr Arg Gly
  1               5                  10                  15

acc atg tcc agg aca aag agt ggt gtt gcc tgt caa aag tgg ggt gcc       96
Thr Met Ser Arg Thr Lys Ser Gly Val Ala Cys Gln Lys Trp Gly Ala
             20                  25                  30

acg ttc ccc cac gta ccc aac tac tct ccc agt aca cat ccc aat gag      144
Thr Phe Pro His Val Pro Asn Tyr Ser Pro Ser Thr His Pro Asn Glu
         35                  40                  45

gga cta gaa gag aac tac tgt agg aac cca gac aat gat gaa caa ggg      192
Gly Leu Glu Glu Asn Tyr Cys Arg Asn Pro Asp Asn Asp Glu Gln Gly
     50                  55                  60

cct tgg tgc tac act aca gat ccg gac aag aga tat gac tac tgc aac      240
Pro Trp Cys Tyr Thr Thr Asp Pro Asp Lys Arg Tyr Asp Tyr Cys Asn
 65                  70                  75                  80

att cct gaa tgt gaa gag gaa tgc atg tac tgc agt gga gaa aag tat      288
Ile Pro Glu Cys Glu Glu Glu Cys Met Tyr Cys Ser Gly Glu Lys Tyr
                 85                  90                  95

gag ggc aaa atc tcc aag acc atg tct gga ctt gac tgc cag gcc tgg      336
Glu Gly Lys Ile Ser Lys Thr Met Ser Gly Leu Asp Cys Gln Ala Trp
            100                 105                 110

gat tct cag agc cca cat gct cat gga tac atc cct gcc aaa ttt cca      384
Asp Ser Gln Ser Pro His Ala His Gly Tyr Ile Pro Ala Lys Phe Pro
        115                 120                 125

agc aag aac ctg aag atg aat tat tgc cac aac cct gac ggg gag cca      432
Ser Lys Asn Leu Lys Met Asn Tyr Cys His Asn Pro Asp Gly Glu Pro
    130                 135                 140

agg ccc tgg tgc ttc aca aca gac ccc acc aaa cgc tgg gaa tac tgt      480
Arg Pro Trp Cys Phe Thr Thr Asp Pro Thr Lys Arg Trp Glu Tyr Cys
145                 150                 155                 160

gac atc ccc cgc tgc aca aca ccc ccg ccc cca ccc agc cca acc tac      528
Asp Ile Pro Arg Cys Thr Thr Pro Pro Pro Pro Pro Ser Pro Thr Tyr
                165                 170                 175

caa tgt ctg aaa gga aga ggt gaa aat tac cga ggg acc gtg tct gtc      576
Gln Cys Leu Lys Gly Arg Gly Glu Asn Tyr Arg Gly Thr Val Ser Val
            180                 185                 190

acc gtg tct ggg aaa acc tgt cag cgc tgg agt gag caa acc cct cat      624
```

```
Thr Val Ser Gly Lys Thr Cys Gln Arg Trp Ser Glu Gln Thr Pro His
        195                 200                 205

agg cac aac agg aca cca gaa aat ttc ccc tgc aaa aat ctg gaa gag      672
Arg His Asn Arg Thr Pro Glu Asn Phe Pro Cys Lys Asn Leu Glu Glu
    210                 215                 220

aac tac tgc cgg aac cca gat gga gaa act gct ccc tgg tgc tat acc      720
Asn Tyr Cys Arg Asn Pro Asp Gly Glu Thr Ala Pro Trp Cys Tyr Thr
225                 230                 235                 240

act gac agc cag ctg agg tgg gag tac tgt gag att cca tcc tgc gag      768
Thr Asp Ser Gln Leu Arg Trp Glu Tyr Cys Glu Ile Pro Ser Cys Glu
                245                 250                 255

tcc tca gca tca cca gac cag tca gat tcc tca gtt cca cca gag gag      816
Ser Ser Ala Ser Pro Asp Gln Ser Asp Ser Ser Val Pro Pro Glu Glu
            260                 265                 270

caa aca cct gtg gtc cag gaa tgc tac cag agc gat ggg cag agc tat      864
Gln Thr Pro Val Val Gln Glu Cys Tyr Gln Ser Asp Gly Gln Ser Tyr
        275                 280                 285

cgg ggt aca tcg tcc act acc atc aca ggg aag aag tgc cag tcc tgg      912
Arg Gly Thr Ser Ser Thr Thr Ile Thr Gly Lys Lys Cys Gln Ser Trp
    290                 295                 300

gca gct atg ttt cca cac agg cat tcg aag acc cca gag aac ttc cca      960
Ala Ala Met Phe Pro His Arg His Ser Lys Thr Pro Glu Asn Phe Pro
305                 310                 315                 320

gat gct ggc ttg gag atg aac tac tgc agg aac ccg gat ggt gac aag     1008
Asp Ala Gly Leu Glu Met Asn Tyr Cys Arg Asn Pro Asp Gly Asp Lys
                325                 330                 335

ggc cct tgg tgc tac acc act gac ccg agc gtc agg tgg gaa tac tgc     1056
Gly Pro Trp Cys Tyr Thr Thr Asp Pro Ser Val Arg Trp Glu Tyr Cys
            340                 345                 350

aac ctg aag cgg tgc tca gag aca gga ggg                             1086
Asn Leu Lys Arg Cys Ser Glu Thr Gly Gly
        355                 360


<210> SEQ ID NO 25
<211> LENGTH: 362
<212> TYPE: PRT
<213> ORGANISM: Mus musculus

<400> SEQUENCE: 25

Val Tyr Leu Ser Glu Cys Lys Thr Gly Ile Gly Asn Gly Tyr Arg Gly
  1               5                  10                  15

Thr Met Ser Arg Thr Lys Ser Gly Val Ala Cys Gln Lys Trp Gly Ala
            20                  25                  30

Thr Phe Pro His Val Pro Asn Tyr Ser Pro Ser Thr His Pro Asn Glu
        35                  40                  45

Gly Leu Glu Glu Asn Tyr Cys Arg Asn Pro Asp Asn Asp Glu Gln Gly
    50                  55                  60

Pro Trp Cys Tyr Thr Thr Asp Pro Asp Lys Arg Tyr Asp Tyr Cys Asn
 65                  70                  75                  80

Ile Pro Glu Cys Glu Glu Glu Cys Met Tyr Cys Ser Gly Glu Lys Tyr
                 85                  90                  95

Glu Gly Lys Ile Ser Lys Thr Met Ser Gly Leu Asp Cys Gln Ala Trp
            100                 105                 110

Asp Ser Gln Ser Pro His Ala His Gly Tyr Ile Pro Ala Lys Phe Pro
        115                 120                 125

Ser Lys Asn Leu Lys Met Asn Tyr Cys His Asn Pro Asp Gly Glu Pro
    130                 135                 140

Arg Pro Trp Cys Phe Thr Thr Asp Pro Thr Lys Arg Trp Glu Tyr Cys
145                 150                 155                 160
```

```
Asp Ile Pro Arg Cys Thr Thr Pro Pro Pro Pro Pro Ser Pro Thr Tyr
                165                 170                 175

Gln Cys Leu Lys Gly Arg Gly Glu Asn Tyr Arg Gly Thr Val Ser Val
            180                 185                 190

Thr Val Ser Gly Lys Thr Cys Gln Arg Trp Ser Glu Gln Thr Pro His
        195                 200                 205

Arg His Asn Arg Thr Pro Glu Asn Phe Pro Cys Lys Asn Leu Glu Glu
    210                 215                 220

Asn Tyr Cys Arg Asn Pro Asp Gly Glu Thr Ala Pro Trp Cys Tyr Thr
225                 230                 235                 240

Thr Asp Ser Gln Leu Arg Trp Glu Tyr Cys Glu Ile Pro Ser Cys Glu
                245                 250                 255

Ser Ser Ala Ser Pro Asp Gln Ser Asp Ser Ser Val Pro Pro Glu Glu
            260                 265                 270

Gln Thr Pro Val Val Gln Glu Cys Tyr Gln Ser Asp Gly Gln Ser Tyr
        275                 280                 285

Arg Gly Thr Ser Ser Thr Thr Ile Thr Gly Lys Lys Cys Gln Ser Trp
    290                 295                 300

Ala Ala Met Phe Pro His Arg His Ser Lys Thr Pro Glu Asn Phe Pro
305                 310                 315                 320

Asp Ala Gly Leu Glu Met Asn Tyr Cys Arg Asn Pro Asp Gly Asp Lys
                325                 330                 335

Gly Pro Trp Cys Tyr Thr Thr Asp Pro Ser Val Arg Trp Glu Tyr Cys
            340                 345                 350

Asn Leu Lys Arg Cys Ser Glu Thr Gly Gly
        355                 360


<210> SEQ ID NO 26
<211> LENGTH: 31
<212> TYPE: DNA
<213> ORGANISM: Artificial Sequence
<220> FEATURE:
<223> OTHER INFORMATION: Description of Artificial Sequence:Forward
      primer for mouse Fc-Angio
<220> FEATURE:
<221> NAME/KEY: CDS
<222> LOCATION: (2)..(49)

<400> SEQUENCE: 26

c ccc aag ctt gtg tat ctg tca gaa tgt aag                             31
  Pro Lys Leu Val Tyr Leu Ser Glu Cys Lys
    1               5                  10


<210> SEQ ID NO 27
<211> LENGTH: 10
<212> TYPE: PRT
<213> ORGANISM: Artificial Sequence
<220> FEATURE:
<223> OTHER INFORMATION: Description of Artificial Sequence: mouse
      Fc-Angio peptide

<400> SEQUENCE: 27

Pro Lys Leu Val Tyr Leu Ser Glu Cys Lys
  1               5                  10


<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence:Reverse
      primer for mouse Fc-Angio
```

<400> SEQUENCE: 28

```
cccctcgagc taccctcctg tctctgagca                                       30


<210> SEQ ID NO 29
<211> LENGTH: 29
<212> TYPE: DNA
<213> ORGANISM: Artificial Sequence
<220> FEATURE:
<223> OTHER INFORMATION: Description of Artificial Sequence:Forward
      primer for canine Fc
<220> FEATURE:
<221> NAME/KEY: CDS
<222> LOCATION: (3)..(29)

<400> SEQUENCE: 29

cc tta agc gaa aat gga aga gtt cct cgc                                 29
   Leu Ser Glu Asn Gly Arg Val Pro Arg
     1               5


<210> SEQ ID NO 30
<211> LENGTH: 9
<212> TYPE: PRT
<213> ORGANISM: Artificial Sequence
<220> FEATURE:
<223> OTHER INFORMATION: Description of Artificial Sequence: canine Fc
      peptide

<400> SEQUENCE: 30

Leu Ser Glu Asn Gly Arg Val Pro Arg
  1               5


<210> SEQ ID NO 31
<211> LENGTH: 40
<212> TYPE: DNA
<213> ORGANISM: Artificial Sequence
<220> FEATURE:
<223> OTHER INFORMATION: Description of Artificial Sequence:Reverse
      primer for canine Fc

<400> SEQUENCE: 31

cctcgagtca tttacccggg gaatgggaga gggatttctg                            40


<210> SEQ ID NO 32
<211> LENGTH: 702
<212> TYPE: DNA
<213> ORGANISM: Canis familiaris
<220> FEATURE:
<221> NAME/KEY: CDS
<222> LOCATION: (1)..(702)
<223> OTHER INFORMATION: Fc

<400> SEQUENCE: 32

gaa aat gga aga gtt cct cgc cca cct gat tgt ccc aaa tgc cca gcc        48
Glu Asn Gly Arg Val Pro Arg Pro Pro Asp Cys Pro Lys Cys Pro Ala
  1               5                  10                  15

cct gaa atg ctg gga ggg cct tcg gtc ttc atc ttt ccc ccg aaa ccc        96
Pro Glu Met Leu Gly Gly Pro Ser Val Phe Ile Phe Pro Pro Lys Pro
             20                  25                  30

aag gac acc ctc ttg att gcc cga aca cct gag gtc aca tgt gtg gtg       144
Lys Asp Thr Leu Leu Ile Ala Arg Thr Pro Glu Val Thr Cys Val Val
         35                  40                  45

gtg gat ctg gga cca gaa gac cct gag gtg cag atc agc tgg ttc gtg       192
Val Asp Leu Gly Pro Glu Asp Pro Glu Val Gln Ile Ser Trp Phe Val
     50                  55                  60

gac ggt aag cag atg caa aca gcc aag act cag cct cgt gag gag cag       240
Asp Gly Lys Gln Met Gln Thr Ala Lys Thr Gln Pro Arg Glu Glu Gln
```

```
 65                  70                  75                  80

ttc aat ggc acc tac cgt gtg gtc agt gtc ctc ccc att ggg cac cag      288
Phe Asn Gly Thr Tyr Arg Val Val Ser Val Leu Pro Ile Gly His Gln
                85                  90                  95

gac tgg ctc aag ggg aag cag ttc acg tgc aaa gtc aac aac aaa gcc      336
Asp Trp Leu Lys Gly Lys Gln Phe Thr Cys Lys Val Asn Asn Lys Ala
            100                 105                 110

ctc cca tcc ccg atc gag agg acc atc tcc aag gcc aga ggg cag gcc      384
Leu Pro Ser Pro Ile Glu Arg Thr Ile Ser Lys Ala Arg Gly Gln Ala
        115                 120                 125

cat cag ccc agt gtg tat gtc ctg ccg cca tcc cgg gag gag ttg agc      432
His Gln Pro Ser Val Tyr Val Leu Pro Pro Ser Arg Glu Glu Leu Ser
    130                 135                 140

aag aac aca gtc agc ttg aca tgc ctg atc aaa gac ttc ttc cca cct      480
Lys Asn Thr Val Ser Leu Thr Cys Leu Ile Lys Asp Phe Phe Pro Pro
145                 150                 155                 160

gac att gat gtg gag tgg cag agc aat gga cag cag gag cct gag agc      528
Asp Ile Asp Val Glu Trp Gln Ser Asn Gly Gln Gln Glu Pro Glu Ser
                165                 170                 175

aag tac cgc acg acc ccg ccc cag ctg gac gag gac ggg tcc tac ttc      576
Lys Tyr Arg Thr Thr Pro Pro Gln Leu Asp Glu Asp Gly Ser Tyr Phe
            180                 185                 190

ctg tac agc aag ctc tct gtg gac aag agc cgc tgg cag cgg gga gac      624
Leu Tyr Ser Lys Leu Ser Val Asp Lys Ser Arg Trp Gln Arg Gly Asp
        195                 200                 205

acc ttc ata tgt gcg gtg atg cat gaa gct cta cac aac cac tac aca      672
Thr Phe Ile Cys Ala Val Met His Glu Ala Leu His Asn His Tyr Thr
    210                 215                 220

cag aaa tcc ctc tcc cat tct ccg ggt aaa                              702
Gln Lys Ser Leu Ser His Ser Pro Gly Lys
225                 230


<210> SEQ ID NO 33
<211> LENGTH: 234
<212> TYPE: PRT
<213> ORGANISM: Canis familiaris

<400> SEQUENCE: 33

Glu Asn Gly Arg Val Pro Arg Pro Pro Asp Cys Pro Lys Cys Pro Ala
  1               5                  10                  15

Pro Glu Met Leu Gly Gly Pro Ser Val Phe Ile Phe Pro Pro Lys Pro
             20                  25                  30

Lys Asp Thr Leu Leu Ile Ala Arg Thr Pro Glu Val Thr Cys Val Val
         35                  40                  45

Val Asp Leu Gly Pro Glu Asp Pro Glu Val Gln Ile Ser Trp Phe Val
     50                  55                  60

Asp Gly Lys Gln Met Gln Thr Ala Lys Thr Gln Pro Arg Glu Glu Gln
 65                  70                  75                  80

Phe Asn Gly Thr Tyr Arg Val Val Ser Val Leu Pro Ile Gly His Gln
                85                  90                  95

Asp Trp Leu Lys Gly Lys Gln Phe Thr Cys Lys Val Asn Asn Lys Ala
            100                 105                 110

Leu Pro Ser Pro Ile Glu Arg Thr Ile Ser Lys Ala Arg Gly Gln Ala
        115                 120                 125

His Gln Pro Ser Val Tyr Val Leu Pro Pro Ser Arg Glu Glu Leu Ser
    130                 135                 140

Lys Asn Thr Val Ser Leu Thr Cys Leu Ile Lys Asp Phe Phe Pro Pro
145                 150                 155                 160
```

```
Asp Ile Asp Val Glu Trp Gln Ser Asn Gly Gln Gln Glu Pro Glu Ser
                165                 170                 175

Lys Tyr Arg Thr Thr Pro Pro Gln Leu Asp Glu Asp Gly Ser Tyr Phe
            180                 185                 190

Leu Tyr Ser Lys Leu Ser Val Asp Lys Ser Arg Trp Gln Arg Gly Asp
        195                 200                 205

Thr Phe Ile Cys Ala Val Met His Glu Ala Leu His Asn His Tyr Thr
    210                 215                 220

Gln Lys Ser Leu Ser His Ser Pro Gly Lys
225                 230


<210> SEQ ID NO 34
<211> LENGTH: 552
<212> TYPE: DNA
<213> ORGANISM: Canis familiaris
<220> FEATURE:
<221> NAME/KEY: CDS
<222> LOCATION: (1)..(552)
<223> OTHER INFORMATION: Endostatin

<400> SEQUENCE: 34

cac acc cac cag gac ttc cag ccg gtg ctg cac ctg gtg gcc ctg aac       48
His Thr His Gln Asp Phe Gln Pro Val Leu His Leu Val Ala Leu Asn
  1               5                  10                  15

agc ccg cag ccg ggc ggc atg cga ggc atc cgg gga gcg gac ttc cag       96
Ser Pro Gln Pro Gly Gly Met Arg Gly Ile Arg Gly Ala Asp Phe Gln
            20                  25                  30

tgc ttc cag cag gcg cgc gcc gcg ggg ctg gcc ggc acc ttc cgg gcc      144
Cys Phe Gln Gln Ala Arg Ala Ala Gly Leu Ala Gly Thr Phe Arg Ala
        35                  40                  45

ttc ctg tcg tcg cgg ctg cag gac ctc tac agc atc gtg cgc cgc gcc      192
Phe Leu Ser Ser Arg Leu Gln Asp Leu Tyr Ser Ile Val Arg Arg Ala
     50                  55                  60

gac cgc acc ggg gtg ccc gtc gtc aac ctc agg gac gag gtg ctc ttc      240
Asp Arg Thr Gly Val Pro Val Val Asn Leu Arg Asp Glu Val Leu Phe
 65                  70                  75                  80

ccc agc tgg gag gcc tta ttc tcg ggc tcc gag ggc cag ctg aag ccc      288
Pro Ser Trp Glu Ala Leu Phe Ser Gly Ser Glu Gly Gln Leu Lys Pro
                 85                  90                  95

ggg gcc cgc atc ttc tct ttc gac ggc aga gat gtc ctg cag cac ccc      336
Gly Ala Arg Ile Phe Ser Phe Asp Gly Arg Asp Val Leu Gln His Pro
            100                 105                 110

gcc tgg ccc cgg aag agc gtg tgg cac ggc tcc gac ccc agc ggg cgc      384
Ala Trp Pro Arg Lys Ser Val Trp His Gly Ser Asp Pro Ser Gly Arg
        115                 120                 125

cgc ctg acc gac agc tac tgc gag acg tgg cgg acg gag gcc ccg gcg      432
Arg Leu Thr Asp Ser Tyr Cys Glu Thr Trp Arg Thr Glu Ala Pro Ala
    130                 135                 140

gcc acc ggg cag gcg tcg tcg ctg ctg gcg ggc agg ctg ctg gag cag      480
Ala Thr Gly Gln Ala Ser Ser Leu Leu Ala Gly Arg Leu Leu Glu Gln
145                 150                 155                 160

gag gcc gcg agc tgc cgc cac gcc ttc gtg gtg ctc tgc atc gag aac      528
Glu Ala Ala Ser Cys Arg His Ala Phe Val Val Leu Cys Ile Glu Asn
                165                 170                 175

agc gtc atg acc tcc ttc tcc aag                                      552
Ser Val Met Thr Ser Phe Ser Lys
            180


<210> SEQ ID NO 35
<211> LENGTH: 184
<212> TYPE: PRT
<213> ORGANISM: Canis familiaris
```

<400> SEQUENCE: 35

```
His Thr His Gln Asp Phe Gln Pro Val Leu His Leu Val Ala Leu Asn
  1               5                  10                  15

Ser Pro Gln Pro Gly Gly Met Arg Gly Ile Arg Gly Ala Asp Phe Gln
             20                  25                  30

Cys Phe Gln Gln Ala Arg Ala Ala Gly Leu Ala Gly Thr Phe Arg Ala
         35                  40                  45

Phe Leu Ser Ser Arg Leu Gln Asp Leu Tyr Ser Ile Val Arg Arg Ala
     50                  55                  60

Asp Arg Thr Gly Val Pro Val Val Asn Leu Arg Asp Glu Val Leu Phe
 65                  70                  75                  80

Pro Ser Trp Glu Ala Leu Phe Ser Gly Ser Glu Gly Gln Leu Lys Pro
                 85                  90                  95

Gly Ala Arg Ile Phe Ser Phe Asp Gly Arg Asp Val Leu Gln His Pro
            100                 105                 110

Ala Trp Pro Arg Lys Ser Val Trp His Gly Ser Asp Pro Ser Gly Arg
        115                 120                 125

Arg Leu Thr Asp Ser Tyr Cys Glu Thr Trp Arg Thr Glu Ala Pro Ala
    130                 135                 140

Ala Thr Gly Gln Ala Ser Ser Leu Leu Ala Gly Arg Leu Leu Glu Gln
145                 150                 155                 160

Glu Ala Ala Ser Cys Arg His Ala Phe Val Val Leu Cys Ile Glu Asn
                165                 170                 175

Ser Val Met Thr Ser Phe Ser Lys
            180
```

<210> SEQ ID NO 36
<211> LENGTH: 41
<212> TYPE: DNA
<213> ORGANISM: Artificial Sequence
<220> FEATURE:
<223> OTHER INFORMATION: Description of Artificial Sequence: HindIII/DraIII linker: top strand
<220> FEATURE:
<221> NAME/KEY: CDS
<222> LOCATION: (3)..(41)

<400> SEQUENCE: 36

```
ag ctt cac acc cac cag gac ttc cag ccg gtg ctg cac ctg                41
   Leu His Thr His Gln Asp Phe Gln Pro Val Leu His Leu
     1               5                  10
```

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence: linker peptide

<400> SEQUENCE: 37

```
Leu His Thr His Gln Asp Phe Gln Pro Val Leu His Leu
  1               5                  10
```

<210> SEQ ID NO 38
<211> LENGTH: 34
<212> TYPE: DNA
<213> ORGANISM: Artificial Sequence
<220> FEATURE:
<223> OTHER INFORMATION: Description of Artificial Sequence: HindIII/DraIII linker: bottom strand

```
<400> SEQUENCE: 38

gtgcagcacc ggctggaagt cctggtgggt gtga                              34


<210> SEQ ID NO 39
<211> LENGTH: 1077
<212> TYPE: DNA
<213> ORGANISM: Canis familiaris
<220> FEATURE:
<221> NAME/KEY: CDS
<222> LOCATION: (1)..(1077)
<223> OTHER INFORMATION: angiostatin

<400> SEQUENCE: 39

ata tat ctt tca gag tgc aag act gga aat ggg aaa acc tac agg ggg      48
Ile Tyr Leu Ser Glu Cys Lys Thr Gly Asn Gly Lys Thr Tyr Arg Gly
  1               5                  10                  15

acc atg gcc aaa acg aag aat gat gtt gcc tgt caa aaa tgg agt gac      96
Thr Met Ala Lys Thr Lys Asn Asp Val Ala Cys Gln Lys Trp Ser Asp
             20                  25                  30

aat tct ccg cac aaa cct aac tat acg cct gag aag cac ccc ttg gag     144
Asn Ser Pro His Lys Pro Asn Tyr Thr Pro Glu Lys His Pro Leu Glu
         35                  40                  45

ggg ctg gag gag aac tat tgc agg aac cct gac aac gac gag aac ggg     192
Gly Leu Glu Glu Asn Tyr Cys Arg Asn Pro Asp Asn Asp Glu Asn Gly
     50                  55                  60

ccc tgg tgc tac acc aca aac cca gac gtg agg ttc gac tac tgc aac     240
Pro Trp Cys Tyr Thr Thr Asn Pro Asp Val Arg Phe Asp Tyr Cys Asn
 65                  70                  75                  80

att cca gaa tgt gaa gag gaa tgt atg cat tgc agt ggg gaa aat tat     288
Ile Pro Glu Cys Glu Glu Glu Cys Met His Cys Ser Gly Glu Asn Tyr
                 85                  90                  95

gag ggc aaa att tcc aag aca aag tct gga ctc gag tgc caa gcc tgg     336
Glu Gly Lys Ile Ser Lys Thr Lys Ser Gly Leu Glu Cys Gln Ala Trp
            100                 105                 110

aac tct caa acc cca cat gct cat gga tat att cct tcc aaa ttt cca     384
Asn Ser Gln Thr Pro His Ala His Gly Tyr Ile Pro Ser Lys Phe Pro
        115                 120                 125

agc aag aac ttg aag atg aat tac tgc cgt aac cct gat ggg gag ccc     432
Ser Lys Asn Leu Lys Met Asn Tyr Cys Arg Asn Pro Asp Gly Glu Pro
    130                 135                 140

cgc cca tgg tgt ttc acc atg gat ccc aac aaa cgc tgg gaa ttc tgt     480
Arg Pro Trp Cys Phe Thr Met Asp Pro Asn Lys Arg Trp Glu Phe Cys
145                 150                 155                 160

gac att ccc cgc tgt aca aca cca cca ccc cct tcg ggc cca acg tac     528
Asp Ile Pro Arg Cys Thr Thr Pro Pro Pro Pro Ser Gly Pro Thr Tyr
                165                 170                 175

cag tgt ctg aag ggc aga ggg gag agc tac cga ggg aag gtg tcc gtc     576
Gln Cys Leu Lys Gly Arg Gly Glu Ser Tyr Arg Gly Lys Val Ser Val
            180                 185                 190

act gtc tct gga cat aca tgt cag cac tgg agt gaa cag acc cct cac     624
Thr Val Ser Gly His Thr Cys Gln His Trp Ser Glu Gln Thr Pro His
        195                 200                 205

aag cac aac agg acc cca gaa aac ttc cct tgc aaa aat ttg gat gaa     672
Lys His Asn Arg Thr Pro Glu Asn Phe Pro Cys Lys Asn Leu Asp Glu
    210                 215                 220

aac tac tgt cgc aac cct gat gga gaa aca gct cca tgg tgc tac aca     720
Asn Tyr Cys Arg Asn Pro Asp Gly Glu Thr Ala Pro Trp Cys Tyr Thr
225                 230                 235                 240

acc aac agt gag gtg agg tgg gaa cac tgc cag att ccg tcc tgt gag     768
Thr Asn Ser Glu Val Arg Trp Glu His Cys Gln Ile Pro Ser Cys Glu
                245                 250                 255
```

```
tcc tct cca ata acc aca gaa tat ttg gat gcc cca gct tca gtg cca       816
Ser Ser Pro Ile Thr Thr Glu Tyr Leu Asp Ala Pro Ala Ser Val Pro
            260                 265                 270

cct gaa caa act cct gtg gtc cag gag tgc tac cac ggc aat ggg cag       864
Pro Glu Gln Thr Pro Val Val Gln Glu Cys Tyr His Gly Asn Gly Gln
        275                 280                 285

agt tat cga ggc aca tca tcc act act atc aca gga aga aaa tgt cag       912
Ser Tyr Arg Gly Thr Ser Ser Thr Thr Ile Thr Gly Arg Lys Cys Gln
    290                 295                 300

tct tgg tca tct atg aca cca cac cga cat gag aag acc cca gaa cac       960
Ser Trp Ser Ser Met Thr Pro His Arg His Glu Lys Thr Pro Glu His
305                 310                 315                 320

ttc ccg gag gct ggc ctg aca atg aac tac tgc agg aat ccc gac gcc      1008
Phe Pro Glu Ala Gly Leu Thr Met Asn Tyr Cys Arg Asn Pro Asp Ala
                325                 330                 335

gac aaa agc cct tgg tgt tac acc acc gac ccc tct gtg cgc tgg gag      1056
Asp Lys Ser Pro Trp Cys Tyr Thr Thr Asp Pro Ser Val Arg Trp Glu
            340                 345                 350

ttc tgt aac ttg aga aaa tgc                                          1077
Phe Cys Asn Leu Arg Lys Cys
        355


<210> SEQ ID NO 40
<211> LENGTH: 359
<212> TYPE: PRT
<213> ORGANISM: Canis familiaris

<400> SEQUENCE: 40

Ile Tyr Leu Ser Glu Cys Lys Thr Gly Asn Gly Lys Thr Tyr Arg Gly
  1               5                  10                  15

Thr Met Ala Lys Thr Lys Asn Asp Val Ala Cys Gln Lys Trp Ser Asp
            20                  25                  30

Asn Ser Pro His Lys Pro Asn Tyr Thr Pro Glu Lys His Pro Leu Glu
        35                  40                  45

Gly Leu Glu Glu Asn Tyr Cys Arg Asn Pro Asp Asn Asp Glu Asn Gly
    50                  55                  60

Pro Trp Cys Tyr Thr Thr Asn Pro Asp Val Arg Phe Asp Tyr Cys Asn
 65                  70                  75                  80

Ile Pro Glu Cys Glu Glu Glu Cys Met His Cys Ser Gly Glu Asn Tyr
                85                  90                  95

Glu Gly Lys Ile Ser Lys Thr Lys Ser Gly Leu Glu Cys Gln Ala Trp
            100                 105                 110

Asn Ser Gln Thr Pro His Ala His Gly Tyr Ile Pro Ser Lys Phe Pro
        115                 120                 125

Ser Lys Asn Leu Lys Met Asn Tyr Cys Arg Asn Pro Asp Gly Glu Pro
    130                 135                 140

Arg Pro Trp Cys Phe Thr Met Asp Pro Asn Lys Arg Trp Glu Phe Cys
145                 150                 155                 160

Asp Ile Pro Arg Cys Thr Thr Pro Pro Pro Ser Gly Pro Thr Tyr
                165                 170                 175

Gln Cys Leu Lys Gly Arg Gly Glu Ser Tyr Arg Gly Lys Val Ser Val
            180                 185                 190

Thr Val Ser Gly His Thr Cys Gln His Trp Ser Glu Gln Thr Pro His
        195                 200                 205

Lys His Asn Arg Thr Pro Glu Asn Phe Pro Cys Lys Asn Leu Asp Glu
    210                 215                 220

Asn Tyr Cys Arg Asn Pro Asp Gly Glu Thr Ala Pro Trp Cys Tyr Thr
225                 230                 235                 240
```

```
Thr Asn Ser Glu Val Arg Trp Glu His Cys Gln Ile Pro Ser Cys Glu
                245                 250                 255

Ser Ser Pro Ile Thr Thr Glu Tyr Leu Asp Ala Pro Ala Ser Val Pro
            260                 265                 270

Pro Glu Gln Thr Pro Val Val Gln Glu Cys Tyr His Gly Asn Gly Gln
        275                 280                 285

Ser Tyr Arg Gly Thr Ser Ser Thr Thr Ile Thr Gly Arg Lys Cys Gln
    290                 295                 300

Ser Trp Ser Ser Met Thr Pro His Arg His Glu Lys Thr Pro Glu His
305                 310                 315                 320

Phe Pro Glu Ala Gly Leu Thr Met Asn Tyr Cys Arg Asn Pro Asp Ala
                325                 330                 335

Asp Lys Ser Pro Trp Cys Tyr Thr Thr Asp Pro Ser Val Arg Trp Glu
            340                 345                 350

Phe Cys Asn Leu Arg Lys Cys
        355


<210> SEQ ID NO 41
<211> LENGTH: 12
<212> TYPE: DNA
<213> ORGANISM: Artificial Sequence
<220> FEATURE:
<223> OTHER INFORMATION: Description of Artificial Sequence:
      palindromic linker where the STOP codon TGA is followed by an
      XhoI site

<400> SEQUENCE: 41

tgactcgagt ca                                                          12


<210> SEQ ID NO 42
<211> LENGTH: 21
<212> TYPE: DNA
<213> ORGANISM: Artificial Sequence
<220> FEATURE:
<223> OTHER INFORMATION: Description of Artificial Sequence:Mutagenic
      primer for murine angiostatin
<220> FEATURE:
<221> NAME/KEY: CDS
<222> LOCATION: (1)..(21)

<400> SEQUENCE: 42

ggg cct tgg agc tac act aca                                            21
Gly Pro Trp Ser Tyr Thr Thr
  1               5


<210> SEQ ID NO 43
<211> LENGTH: 7
<212> TYPE: PRT
<213> ORGANISM: Artificial Sequence
<220> FEATURE:
<223> OTHER INFORMATION: Description of Artificial Sequence: mutagen
      peptide

<400> SEQUENCE: 43

Gly Pro Trp Ser Tyr Thr Thr
  1               5


<210> SEQ ID NO 44
<211> LENGTH: 34
<212> TYPE: DNA
<213> ORGANISM: Artificial Sequence
<220> FEATURE:
<223> OTHER INFORMATION: Description of Artificial Sequence:primer
      used to introduce HindIII into murine angiostatin
<220> FEATURE:
```

```
<221> NAME/KEY: CDS
<222> LOCATION: (9)..(32)

<400> SEQUENCE: 44

gcggatcc aag ctt agt aca cat ccc aat gag gg                          34
         Lys Leu Ser Thr His Pro Asn Glu
           1               5


<210> SEQ ID NO 45
<211> LENGTH: 8
<212> TYPE: PRT
<213> ORGANISM: Artificial Sequence
<220> FEATURE:
<223> OTHER INFORMATION: Description of Artificial Sequence: HindIII
      peptide

<400> SEQUENCE: 45

Lys Leu Ser Thr His Pro Asn Glu
  1               5


<210> SEQ ID NO 46
<211> LENGTH: 59
<212> TYPE: DNA
<213> ORGANISM: Artificial Sequence
<220> FEATURE:
<223> OTHER INFORMATION: Description of Artificial Sequence:BspHI/
      BamHI linker: top strand
<220> FEATURE:
<221> NAME/KEY: CDS
<222> LOCATION: (2)..(58)

<400> SEQUENCE: 46

c atg acc tct ttc tcc aaa tcg agc ggg ggc agc ggg ggc gga ggc agc     49
  Met Thr Ser Phe Ser Lys Ser Ser Gly Gly Ser Gly Gly Gly Gly Ser
    1               5                  10                  15

ggc ggg ggc g                                                        59
Gly Gly Gly


<210> SEQ ID NO 47
<211> LENGTH: 19
<212> TYPE: PRT
<213> ORGANISM: Artificial Sequence
<220> FEATURE:
<223> OTHER INFORMATION: Description of Artificial Sequence: linker
      peptide

<400> SEQUENCE: 47

Met Thr Ser Phe Ser Lys Ser Ser Gly Gly Ser Gly Gly Gly Gly Ser
  1               5                  10                  15

Gly Gly Gly


<210> SEQ ID NO 48
<211> LENGTH: 59
<212> TYPE: DNA
<213> ORGANISM: Artificial Sequence
<220> FEATURE:
<223> OTHER INFORMATION: Description of Artificial Sequence:BspHI/BamHI
      linker: bottom strand

<400> SEQUENCE: 48

gatccgcccc cgccgctgcc tccgcccccg ctgcccccgc tcgatttgga gaaagaggt      59


<210> SEQ ID NO 49
<211> LENGTH: 12
<212> TYPE: DNA
<213> ORGANISM: Artificial Sequence
<220> FEATURE:
<223> OTHER INFORMATION: Description of Artificial Sequence:
```

```
      BamHI/HindIII linker: top strand
<220> FEATURE:
<221> NAME/KEY: CDS
<222> LOCATION: (3)..(11)

<400> SEQUENCE: 49

ga tcc tca ggc c                                                    12
   Ser Ser Gly
     1


<210> SEQ ID NO 50
<211> LENGTH: 12
<212> TYPE: DNA
<213> ORGANISM: Artificial Sequence
<220> FEATURE:
<223> OTHER INFORMATION: Description of Artificial Sequence:
      BamHI/HindIII linker: bottom strand

<400> SEQUENCE: 50

agctggcctg ag                                                       12


<210> SEQ ID NO 51
<211> LENGTH: 10
<212> TYPE: DNA
<213> ORGANISM: Artificial Sequence
<220> FEATURE:
<223> OTHER INFORMATION: Description of Artificial Sequence:
      AflII/HindIII linker: top strand
<220> FEATURE:
<221> NAME/KEY: CDS
<222> LOCATION: (1)..(9)

<400> SEQUENCE: 51

tta agc ggc c                                                       10
Leu Ser Gly
  1


<210> SEQ ID NO 52
<211> LENGTH: 10
<212> TYPE: DNA
<213> ORGANISM: Artificial Sequence
<220> FEATURE:
<223> OTHER INFORMATION: Description of Artificial Sequence:
      AflII/HindIII linker: bottom strand

<400> SEQUENCE: 52

agctgggcgc                                                          10


<210> SEQ ID NO 53
<211> LENGTH: 11
<212> TYPE: DNA
<213> ORGANISM: Artificial Sequence
<220> FEATURE:
<223> OTHER INFORMATION: Description of Artificial Sequence:XhoI/AflII
      linker: top strand
<220> FEATURE:
<221> NAME/KEY: CDS
<222> LOCATION: (3)..(11)

<400> SEQUENCE: 53

tc gac tcc ggc                                                      11
   Asp Ser Gly
     1


<210> SEQ ID NO 54
<211> LENGTH: 11
<212> TYPE: DNA
<213> ORGANISM: Artificial Sequence
<220> FEATURE:
<223> OTHER INFORMATION: Description of Artificial Sequence:XhoI/AflII
```

-continued

```
      linker: bottom strand

<400> SEQUENCE: 54

ttaagccgga g                                                          11
```